(12) United States Patent
Kinmon et al.

(10) Patent No.: US 8,888,826 B2
(45) Date of Patent: Nov. 18, 2014

(54) SURGICAL DEVICE, SYSTEM AND METHOD OF USE THEREOF

(75) Inventors: Kyle Kinmon, Boca Raton, FL (US); Daniel Helme, Pompano Beach, FL (US)

(73) Assignee: Mbrace, LLC, Boca Raton, FL (US)

( * ) Notice: Subject to any disclaimer, the term of this patent is extended or adjusted under 35 U.S.C. 154(b) by 1261 days.

(21) Appl. No.: 12/690,053

(22) Filed: Jan. 19, 2010

(65) Prior Publication Data

US 2010/0125301 A1    May 20, 2010

Related U.S. Application Data

(63) Continuation-in-part of application No. 12/275,133, filed on Nov. 20, 2008.

(51) Int. Cl.
| | |
|---|---|
| *A61B 17/80* | (2006.01) |
| *A61B 17/84* | (2006.01) |
| *A61F 2/08* | (2006.01) |
| *A61B 17/064* | (2006.01) |
| *A61B 17/17* | (2006.01) |
| *A61B 17/00* | (2006.01) |
| *A61B 17/22* | (2006.01) |

(52) U.S. Cl.
CPC ......... *A61B 17/0642* (2013.01); *A61B 17/8004* (2013.01); *A61B 17/8009* (2013.01); *A61B 17/1757* (2013.01); *A61B 17/1728* (2013.01); *A61B 17/1739* (2013.01); *A61B 17/8023* (2013.01); *A61B 17/8061* (2013.01); *A61B 2017/00407* (2013.01); *A61B 2017/00867* (2013.01); *A61B 2017/22038* (2013.01); *A61B 17/8095* (2013.01); *A61B 2017/1775* (2013.01)

USPC ........... 606/300; 606/301; 606/304; 606/320; 606/328; 606/75

(58) Field of Classification Search
USPC .................... 606/75, 300, 301, 304, 320, 328
See application file for complete search history.

(56) References Cited

U.S. PATENT DOCUMENTS

| | | |
|---|---|---|
| 3,960,147 A | 6/1976 | Murray |
| 4,414,967 A | 11/1983 | Shapiro |
| 4,913,144 A | 4/1990 | Del Medico |
| 5,053,038 A | 10/1991 | Sheehan |
| 5,662,655 A | 9/1997 | Laboureau |
| 5,779,707 A | 7/1998 | Bertholet |
| 5,785,713 A | 7/1998 | Jobe |
| 6,059,787 A | 5/2000 | Allen |
| 6,179,840 B1 | 1/2001 | Bowman |
| 6,348,054 B1 | 2/2002 | Allen |
| 6,402,757 B1 | 6/2002 | Moore |

(Continued)

*Primary Examiner* — Nicholas Woodall
*Assistant Examiner* — Christine Nelson
(74) *Attorney, Agent, or Firm* — Trojan Law Offices

(57) ABSTRACT

The present invention includes a surgically implantable device, system, and method of use thereof for the internal compression or distraction of, for example, bone fractures, fusions, and osteotomies. More specifically, the surgical device comprises a bridge with one or more adjustable anti-reversing portions. The adjustable anti-reversing portion(s) may be located in a symmetrical or asymmetrical manner on the bridge between the device's legs. The adjustable anti-reversing portion(s) allow for stronger compression of the bone at a known amount of compression. The adjustable anti-reversing portion(s) can also maintain the device's legs in closer proximity to one another for greater compression or maintain the device's legs apart from one another for distraction. The surgical device can also comprise cannulated or grooved legs. A system and method of use is also described.

21 Claims, 28 Drawing Sheets

(56) References Cited

U.S. PATENT DOCUMENTS

| | | |
|---|---|---|
| 6,592,587 B1 | 7/2003 | Roger |
| 6,783,531 B2 | 8/2004 | Allen |
| 7,214,232 B2 | 5/2007 | Bowman |
| 2002/0103489 A1 | 8/2002 | Ku |
| 2003/0167072 A1 | 9/2003 | Oberlander |
| 2007/0093839 A1 | 4/2007 | Beckendorf |
| 2007/0276388 A1 | 11/2007 | Robertson |
| 2008/0234739 A1 * | 9/2008 | Hudgins et al. ............... 606/255 |
| 2009/0062799 A1 | 3/2009 | Holsten et al. |
| 2010/0125275 A1 | 5/2010 | Kinmon et al. |

* cited by examiner

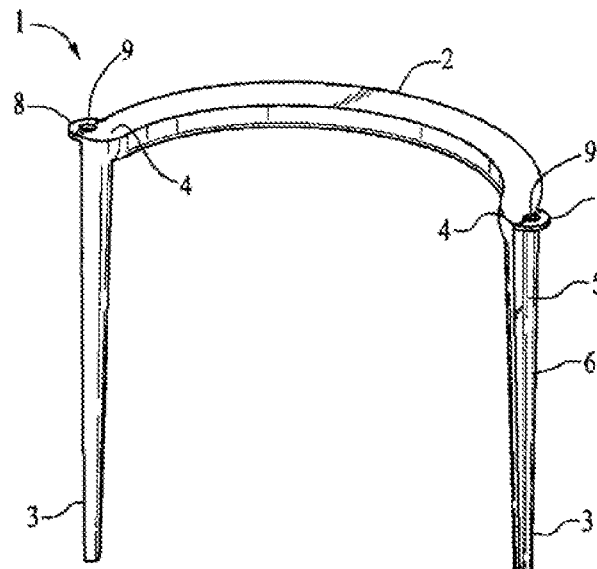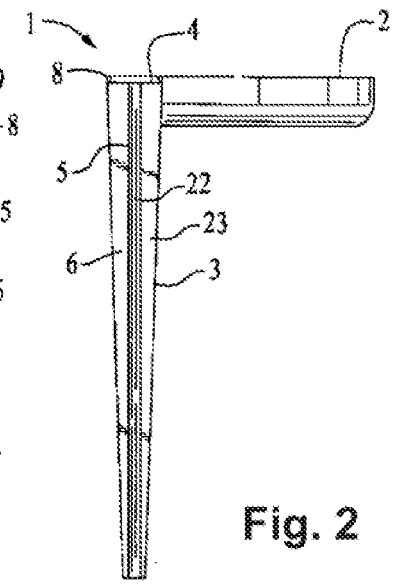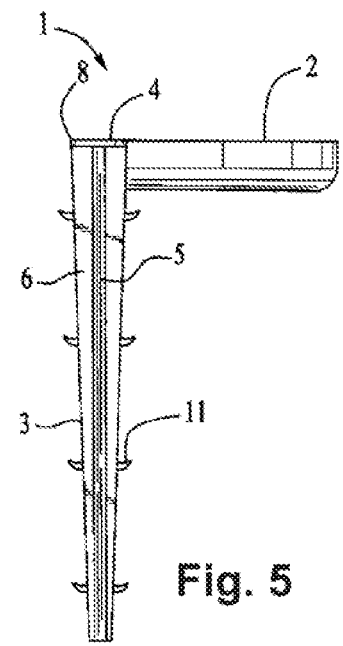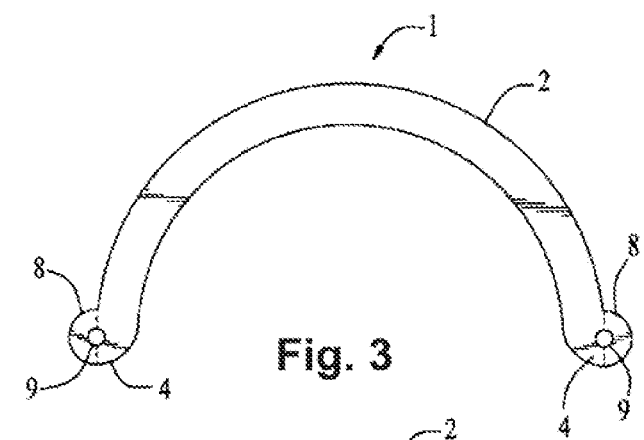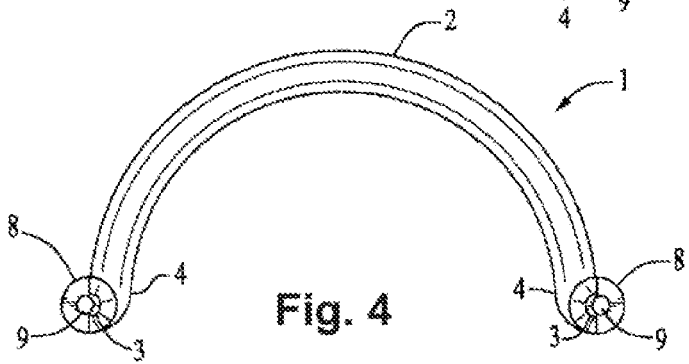

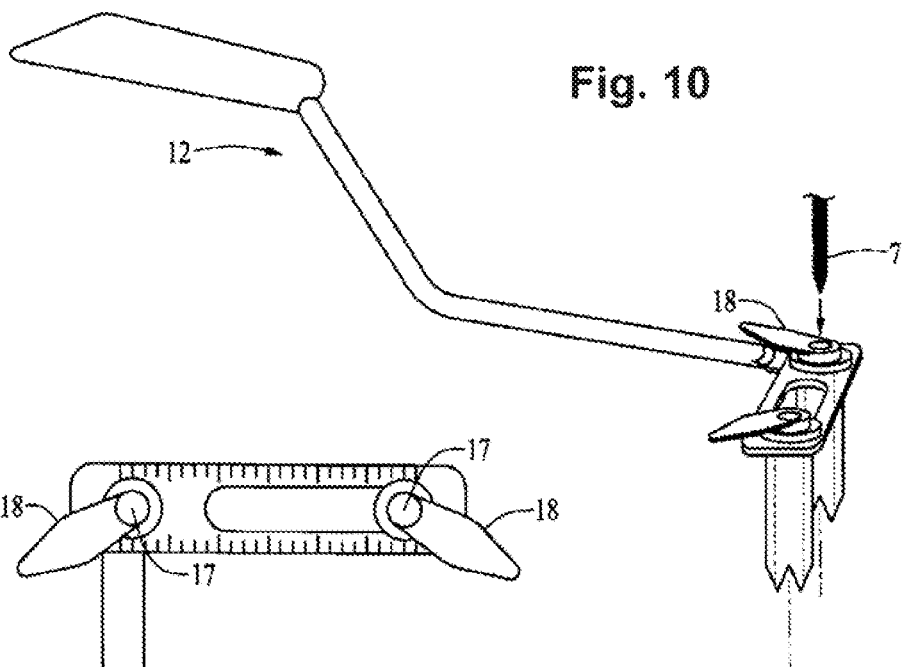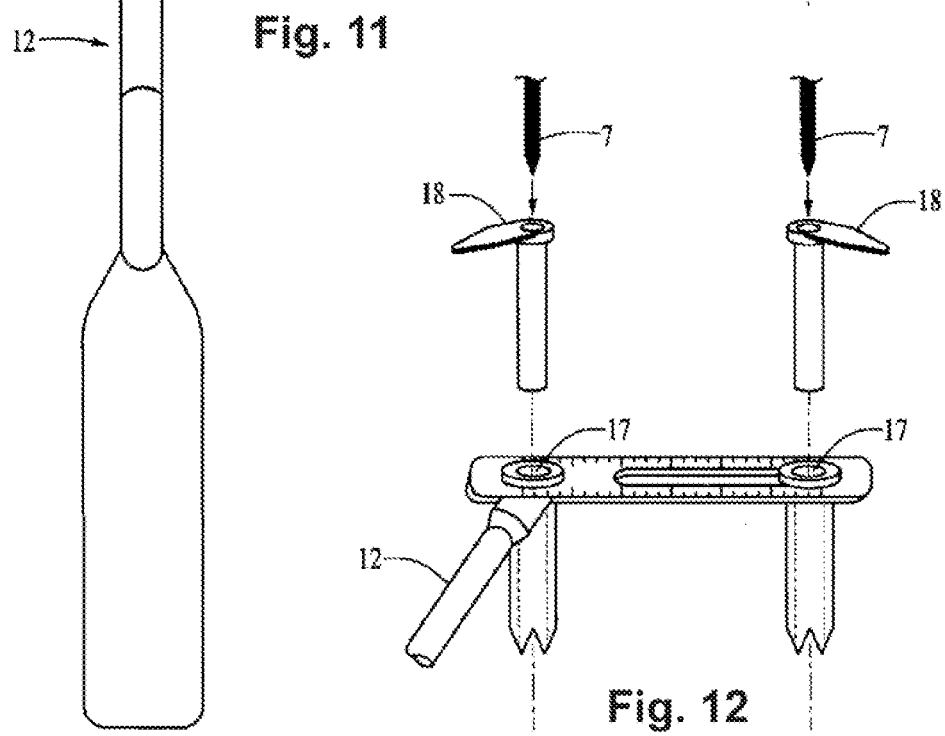

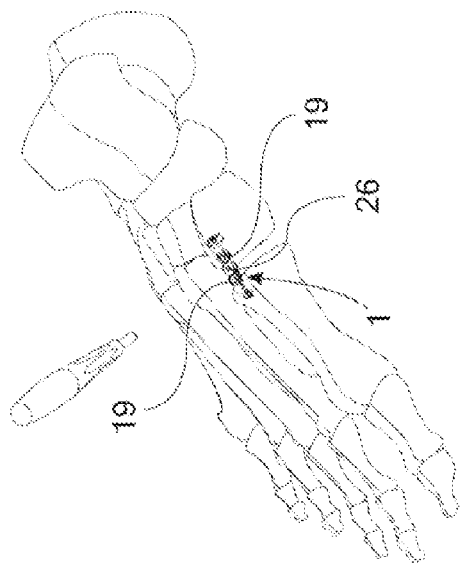
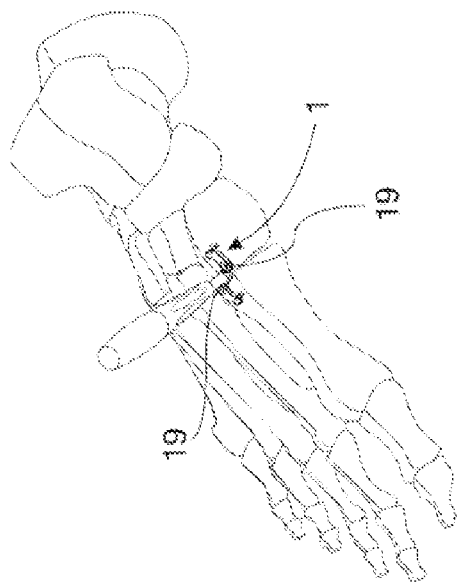
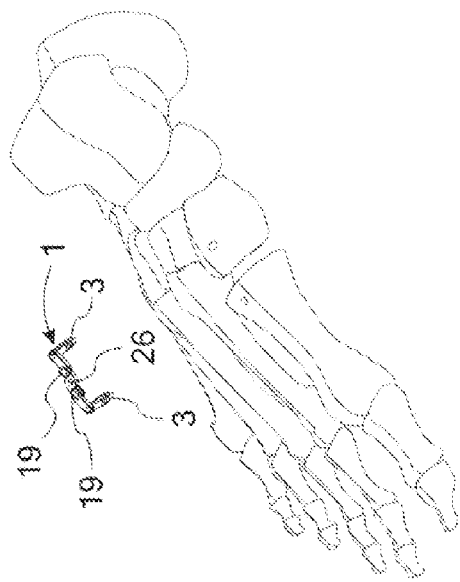
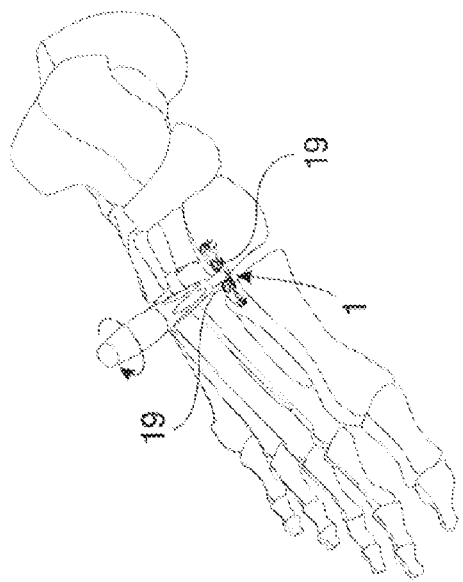
Fig. 39A
Fig. 39B
Fig. 39C
Fig. 39D

SURGICAL DEVICE, SYSTEM AND METHOD OF USE THEREOF

CROSS-REFERENCE TO RELATED APPLICATIONS

This application is a continuation-in-part application of and claims priority to U.S. application Ser. No. 12/275,133, filed on Nov. 20, 2008, which is hereby incorporated by reference in its entirety.

FIELD OF THE INVENTION

The present invention relates to a surgical device, system, and method of use thereof. More specifically, the invention relates to a surgical device with at least one adjustable anti-reversing bridge portion, related tools, and a method for its easy insertion into bone or tissue during orthopedic surgical procedures.

BACKGROUND OF THE INVENTION

Surgical devices used to stabilize bones during orthopedic surgical procedures, such as compression staples, are well known in the art. To correct and heal bone fractures properly, staples are often used to keep bone fragments in position by holding and compressing the bone fragments together without motion. Various staples have been produced to provide compression in various manners.

For example, U.S. Pat. Nos. 6,059,787, 6,348,054, 6,783,531 describe surgical staples and methods that use a spring-type force to create a compression effect. The staples disclosed in these patents require the spreading apart of the staples' legs to create a spring-type force before applying a percussive force to drive the staples into the bone with a resultant compressive effect. Similarly, U.S. Pat. No. 5,785,713 discloses a staple, which has the staple's legs in an initial angled orientation, and the legs must be spread apart to a parallel configuration before inserting the staple into bone. However, fractures may arise from driving the compound-shaped legs into the bone. Also, the mechanism employed for such staples is less than optimal in that the staple's legs converge at their ends to create compression, which provides little to no compression at the bridge end of the staple.

U.S. Patent Application Publication No. 2007/0276388 discloses surgical staples and annulus closure tools, having two to four legs, for sealing inter-vertebral disk incisions or herniations. A disadvantage of all of the aforementioned staples is that the percussive force applied to drive the staples is quite abrasive and a more controllable method of insertion would be a more advantageous surgical technique. Also, there is no guidance prior to insertion for the precise placement of the staples.

U.S. Pat. No. 4,994,063 describes a method and bone staple for interosseous bone compression. Such staples and methods, however, have common insertion techniques that are extremely difficult to complete. A typical technique initially requires drilling holes for a staple using a drill guide. The drill guide is removed before inserting the staple. In many cases the holes are lost due to blood, debris, and soft issue in the surrounding area that fill into the holes. Thus, it is difficult to accurately assess the location of the holes under fluoroscopy using this technique. For these reasons, staples are placed inaccurately and the holes must be re-drilled to properly insert the staple and repair the bone.

As an attempt to overcome this problematic insertion technique in the field, surgical devices that may be cannulated and used with guides have been introduced. However, such attempts are problematic for other reasons. For example, U.S. Patent Application Publication No. 2007/0093839 describes a compression staple for securing tissue. The two legs of the staple may be cannulated and the reference teaches the following method of insertion: a first guide pin is driven into the first tissue; one of the legs of the staple is inserted over the first guide pin; the staple is aligned in the desired position; a second guide pin is driven into the second tissue; the second staple leg is inserted over the second guide pin, and finally; the staple is driven into the tissue. The prior art fails to teach an easy method of insertion that provides for precise placement of both legs of the staple at the same time. Further, predrilled holes are not used for placement of the staple and the staple must be driven into the bone with percussive force. Another disadvantage of cannulated staples is that they have hollow anchoring members and thus provide a weak structure for purposes of holding bone fragments together. The current devices do not disclose a robust staple or an insertion technique that is precise, quick, not destructive to the bone, and easy.

Therefore, what is needed in the art is an improved surgical staple with increased strength and an improved method that allows for easy and precise insertion into bones or tissues compared with the current methodologies known in the art. With these goals in mind, the inventor has created a robust staple with improved structural properties and compression capabilities, as well as an easy and effective insertion technique and system thereof for stabilizing bones with compression staples during orthopedic and podiatric type surgical procedures.

Surgical devices having a bridge portion that is adjustable so the staple's legs can be adjusted to the better fit and fix bones angled in various positions at a known amount of compression are also not disclosed in the prior art. Nor does the prior art disclose staples that can be easily used for distraction, e.g., maintaining an osteotomy open for re-alignment of bones. The prior art describes staples in which the bridge can be expanded lengthwise to change the distance between the legs of the staples. For example, U.S. Patent Application Publication Nos. 2009/0062799 and 2002/0103489 describe staples in which the length of the bridge can be adjusted. U.S. Pat. No. 4,913,144 discloses a staple in which the position of the staple's legs can be moved towards or away from each other by a dovetail joint on the bridge. The dovetail joint allows for movement of the staple's legs only in this manner. The prior art also does not disclose a device that is capable of maintaining compression at a known amount for a set amount of time. Further, the staples known in the prior art do not include detached legs that can be assembled with the bridge of the staple.

Thus, what is needed is a device with a bridge having one or more adjustable anti-reversing portions on the bridge that allow for not only repositioning of the distance and angle between the legs of the staple, but also the angle of the bridge of the staple itself while maintaining compression or distraction of bones. What is also needed is a device with a bridge having one or more adjustable anti-reversing portions so that the device maintains the compression or distraction. With these goals in mind, the inventor has created a device having a bridge with one or more adjustable anti-reversing portions that allow for independent positioning of the legs of the device, based on the angle in which the adjustable anti-reversing portion(s) are positioned. Moreover, the device described herein maintains a known amount of compression after adjustment of the adjustable anti-reversing portion(s).

The inventor has also created a device with legs detached from the device's bridge and a device which can be dissembled for easy removal.

SUMMARY OF THE INVENTION

The present invention describes a grooved and tabbed compression staple. The invention also describes a system of tools for its insertion into bone as well as a method for its insertion. In one embodiment, the surgical staple for fastening bones, tissues, or fragments thereof, comprises a bridge having a first leg and a second leg extending from a same side of the bridge. Each leg has at least an inner elevation and an outer elevation along its length. The legs are capable of receiving a guide wire between the inner and said outer elevations such that said staple is guided by said guide wires when a user inserts said staple over said guide wires and into bone or tissue during a surgical procedure. The bridge can further comprise a first and second tab extending therefrom, wherein each tab has an aperture therethrough so that the legs and tabs of the staple are capable of receiving a guide wire such that said staple is guided by said guide wires when a user inserts said staple over said guide wires and into bone or tissue during a surgical procedure.

The surgical staple can also be described as comprising a middle bridge portion, having a first end and a second end, a first leg extending from said first end of the bridge, and a second leg extending from said second end of the bridge. The first and second legs each have at least two elevations along the length of each leg. Optionally, tabs extend from each of the middle bridge portion, wherein each tab includes a hole therethrough. The optional tabs can also extend down the length of staple, thereby forming a hole through the length of each staple leg. These tabs that extend down the length of the staple need not extend down the length of each leg in its entirety. The first and second legs and the optional tabs of the staple are capable of aligning with and receiving a guide wires such that the staple is guided by the guide wires when a user inserts the staple over the guide wires and into bone or tissue during a surgical procedure.

In another embodiment, the staple's legs are oriented in a substantially parallel position. In yet another embodiment, the staple's legs are oriented in a converging position. The at least two elevations of each staple leg can be formed along the outer or inner edge of each leg. The staple can be made of a material selected from a group consisting of memory metal, memory alloy, metal material, alloy, and a material capable of being manually compressed by the user.

The bridge of the staple can be curved in an upwards or sideways direction so that the bridge is either parallel or perpendicular to the staple's legs, respectively. In an alternative embodiment, the bridge forms a substantially circular shape and is perpendicular to the staple's legs. The staple's legs can have a plurality of projections protruding therefrom.

A surgical device system is also disclosed, comprising any embodiments of the surgical staple as described above, a plurality of guide wires, and a drill. The drill has a drill bit with a hole axially running through it. A user can insert the guide wires into bone fragments, place the drill bit over the guide wires and thereby receive the wire through the hole in the drill bit to bore holes around the guide wires and into the bone fragments, remove the drill, insert the surgical staple over said guide wires and into said holes in the bone, and remove the guide wires, so as to insert the surgical staple into the bone fragments to repair a bone fracture.

In another embodiment, the surgical device system can include a guide device, whereby a user can place the guide device in a desired position over a bone fracture, insert at least one guide wire through the guide device and into bone fragments, remove the guide device, place the drill bit over the guide wires and thereby receive the wire through the hole in the drill bit to bore holes around the guide wires and into the bone fragments, remove the drill, insert the surgical staple over the guides wires and into said holes in said bone, and remove the guide wires, thereby inserting the surgical staple into the bone fragments to repair the bone fracture. The guide device can include an assembly that is capable of inserting two guide wires at a predetermined width, wherein the width of the assembly is adjustable, and a user can select a desired width to guide insertion of the guide wires into bone.

The guide device can include an adjustable assembly, wherein said adjustable assembly further comprises at least one aperture capable of accepting a drill, and wherein said apertures further comprise detachably attachable inserts capable of accepting at least one guide wire. The user can place the guide device in a desired position over a bone fracture, adjust the positions of the apertures having inserts attached to guide insertion of said guide wires into bone. The user can then insert guide wires through these inserts of the apertures and into bone fragments and remove the inserts while leaving the guide device in place. The user can then use the guide device to accept a drill therethrough, wherein the drill has a drill bit with a hole running axially through it, and can thus place the drill bit over the guide wires to bore holes around the guide wires and into the bone fragments. After the holes are drilled, the drill and guide device can be removed so that the staple can be inserted over the guide wires and into the bone. Afterwards, the user can remove the guide wires, thereby inserting the staple into the bone fragments and repairing a bone fracture.

In yet another embodiment, the system can include a depth gauge, whereby a user can measure the length of the guide wire's insertion and thereby select a desired length of the staple's legs for insertion into bone. The system can also include a staple compression device, whereby a user can insert the staple compression device into the holes of the tabs of the staple and thereby compress the staple's legs towards one another to further aid compression of the surgical staple. A device, such as a tamp or mallet can be used to seat the staple into bone.

A method for using a surgical staple is also disclosed. According to the method, the practitioner places two guide wires in bone, in a desired position on each side of a bone fracture. Holes are bored into the bone fragments over the two guide wires, a grooved and tabbed surgical staple is aligned with the guide wires and inserted into the holes in the bone. The guide wires are removed and the staple is compressed so that the staple stabilizes the bone fragments to repair a bone fracture. The insertion of the guide wires can be aided by placing a guide device over the bone fracture. The holes in the bone can be bored with a cannulated drill placed over the guide wires and the guide wires' positions can be confirmed fluoroscopically. Further, a depth gauge can be used to measure the exposed length of the inserted guide wires to determine the length of the staple's legs to be used. A device such as a mallet or tamp can be used to seat the inserted grooved and tabbed surgical staple and the staple's position can be confirmed fluoroscopically.

In another embodiment, the surgical device further comprises a bridge having one or more adjustable anti-reversing portions for compression or distraction of a first body part relative to a second body part. The device comprises a bridge having a first aperture and second aperture and at least one adjustable anti-reversing portion between the first aperture and second aperture, and a first leg and second leg. The first leg can be inserted through the first aperture and into a first body part, and the second leg can be inserted through the second aperture and into a second body part. The adjustable anti-reversing portion(s) can provide a known amount of compression or distraction of the first and second body parts when the staple is surgically implanted. The device can further comprise an aperture positioned between two adjustable anti-reversing portions that is capable of receiving an instrument, whereby a user can insert the instrument into the aperture and adjust the adjustable anti-reversing portions to provide compression or distraction. The adjustable anti-reversing portion can be comprised of a hinged system, a one-way sliding track system, a ratchet system, a gear and pawl system, a rack and pinion system, a one-way clutch system, or any other anti-reversing mechanism. Further, the first and second legs can be cannulated so that guide wires can guide the device during its insertion.

In yet another embodiment, the surgical device for compression or distraction of a first body part relative to a second body part comprises a bridge having a first leg and a second leg extending from a same side of the bridge. The first leg can be inserted into a first body part and the second leg can be inserted into a second body part. The bridge further comprises at least one adjustable anti-reversing portion. The adjustable anti-reversing portion(s) can provide a known amount of compression or distraction of the first and second body parts when the staple is surgically implanted. This embodiment of the device can further comprise an aperture positioned between two adjustable anti-reversing portions in the bridge or at least one aperture in the adjustable anti-reversing portion that is capable of receiving an instrument, whereby a user can insert the instrument into the aperture and adjust the adjustable anti-reversing portions to provide compression or distraction. The adjustable anti-reversing portion of this embodiment can be comprised of a hinged system, a one-way sliding track system, a ratchet system, a gear and pawl system, a rack and pinion system, a one-way clutch system, or any other anti-reversing mechanism. Further, the first and second legs can be grooved or cannulated so that guide wires can guide the staple during its insertion.

In another embodiment, the device can be comprised of more than one bridge portions attached with one another by an assembly screw. Each bridge portion is attached with a first leg and a second leg such that, once the device is inserted into a body part, the assembly screw can be removed to thereby individually remove each staple leg from the body part.

When the adjustable anti-reversing portion is a one-way sliding track system, the device can also include more than one bridge portion and at least one connecting element. The connecting element in this embodiment allows the bridge portions to move linearly with respect to one another.

A system and method for compression or distraction using the surgical device including one or more adjustable anti-reversing portions is also described herein.

BRIEF DESCRIPTION OF THE DRAWINGS

FIG. 1 is a side perspective view of a surgical staple according to the present invention;

FIG. 2 is a side orthogonal view of a surgical staple according to the present invention;

FIG. 3 is a top orthogonal view of a surgical staple according to the present invention;

FIG. 4 is a bottom orthogonal view of a surgical staple according to the present invention;

FIG. 5 is a side orthogonal view of one embodiment of a surgical staple according to the present invention;

FIG. 10 is a side perspective view of a guide device according to the present invention;

FIG. 11 is a top orthogonal view of a guide device according to the present invention;

FIG. 12 is a side perspective view of an adjustable assembly of a guide device according to the present invention;

FIGS. 39A-39D illustrate insertion of a surgical device having two adjustable anti-reversing portions for compression according to the present invention;

DETAILED DESCRIPTION OF THE INVENTION

Figure 6A:
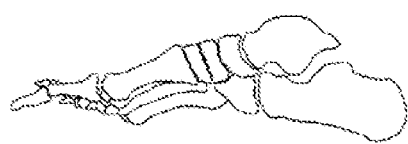
FIGS. 6A-6I depict a system and steps of a method for inserting a surgical staple for repairing bone fractures in accordance with the present invention.

The present invention overcomes disadvantages of the prior art, as identified and disclosed by the inventor, by providing an improved compression staple and an easy-to-use system and method for its insertion for the internal fixation of bone fractures, fusions, and osteotomies. More specifically, the present invention includes a robust grooved and tabbed surgically implantable staple and can be easily inserted over guide wires and across a fractured bone to provide stability and compression across the desired site. The compression staple can be made of a shape memory metal material or alloy, such as nickel titanium, or another metal material or alloy, such as stainless steel or titanium. The staple is preferably made of a non-corrodable metal material compatible with use in the body. The staple may also be made of a bio-absorbable material. Other materials used for bone fixation include vitalium, chrome cobalt, and suitable bio-compatible polymeric materials.

Different embodiments of the staple 1 are illustrated in FIGS. 1-5. As shown in FIG. 1, the staple 1 includes a bridge 2, e.g., a middle bridge portion, and two legs 3 at each end 4 of the bridge portion 2 that extend substantially perpendicular to the middle bridge portion 2. The legs 3 of the staple 1 can be formed in any shape, including, but not limited to, a flat shape or a circular shape. Because the staple's legs 3 can be substantially parallel, the compression is more evenly distributed throughout the staple, whereas staples like those in the prior art that have legs converging towards one another provide little to no compression at the bridge 2 end of the staple 1. The legs 3 of the staple can also be converging towards one another, especially when using a staple 1 made from a shape memory material. The legs 3 of the staple 1 are substantially solid and have at least two elevations, an inner elevation 22 and an outer elevation 23, that run down the length of each staple leg 3. The inner elevation 22 can be defined as the inner most surface of the leg 3. The outer elevation 23 can be defined as the outer most surface of the leg 3.

As shown in FIG. 1, the inner elevation and outer elevation can form U-shaped grooves 5 that run down the entire length of each staple leg 3, however, it is not necessary that a U-shaped groove be formed nor that the grooves 5 be formed along the entire length of each staple leg 3. The inner elevation and outer elevation can also form an L-shaped groove 5 along the length of each staple leg 3 (not shown). The bridge-to-leg interface 4 is solid, therefore the staple 1 avoids any problems of weakness or breakage in the staple's legs 3 or bridge-to-leg interface 4 that hollow or cannulated staple legs can create. The legs 3 of the staple 1 can be tapered or not tapered towards the ends of the legs 3 that are distal from the bridge 2. Also, the distal ends of legs 3 of the staple can be blunt or formed to an acute point.

The grooves 5 that run down the length of each leg 3 of the staple can run down the outer edges 6 of the legs 3. Alternatively, the grooves 5 can run down the inner edges of each of the legs 3 (not shown). The grooves 5 can also be described as a recess. The function of the groove 5 is served so long as the leg 3 has at least two elevations relative to the central axis of the leg.

The efficiency and effectiveness of orthopedic stapling is considerably improved when the staple 1 and associated instruments are used in conjunction with guide wires 7. Accordingly, the shape and diameter of the grooves 5 coincide with the shape and diameter of the guide wires 7 in which the staple 1 is inserted over. For example, as illustrated in FIG. 1, the grooves 5 are in a semi-circular shape. In addition, at each end 4 of the bridge 2 of the staple 1 is a tab 8 with a hole 9 in each tab 8 equal to or greater than the diameter to that of the guide wire 7. Like the grooves 5 of the staple 1, the hole 9 in each tab 8 is sized to accommodate a guide wire 7, and is oriented directly above the groove 5 in the outer edge 6 of each of the staple's legs 3.

Alternatively, in embodiments not shown, the staple 1 can be formed without the tabs 8 or can be formed with the tabs 8 extending downward along the entire length of each staple leg 3. In the latter embodiment, each tab 8 essentially forms an outer edge 6 of each staple leg 3 so that a hole forms axially through the entire length of each staple leg 3. The resulting holes in the staple's legs 3 are capable of receiving guide wires 7 just as the recesses or grooves 5 of the staple 1 are.

Initially, a surgeon can insert guide wires 7 into bone, which remain in place while holes are drilled around the guide wires 7 using a specialized drill 10 that is capable of receiving the guide wires 7 through its drill bit. The staple 1 is subsequently aligned with the guide wires 7 and inserted into the drilled holes.

The staple's holes 9 in its tabs 8 and grooves 5 along its legs 3 are sized to accommodate the passage of guide wires 7 while inserting the staple 1. The diameters of the holes 9, grooves 5, and guide wires 7 can vary depending on the surgical procedure but should be complimentary to each other. The staple 1 can be inserted over or along the guide wires 7 by placing the holes 9 in the tabs 8 over the wires 7, which automatically positions the grooves 5 along the legs 3 of the staple 1 to slide axially down the wires 7. Alternatively, for embodiments of the staple 1 which do not include tabs 8, the grooves 5 are aligned with the guide wires 7 and are sized to accommodate passage of the guide wires 7 for their insertion into the holes drilled around the guide wires 7. Similarly, for the embodiment of the staple 1 in which each tab 8 extends down the edge of each staple leg 3, thereby creating a hole along each staple leg 3, the hole 9 in each tab 8 is sized to receive a guide wire 7 therethrough. These methods prevent the loss of the pre-drilled holes in the bones prior to insertion of the staple 1, which could otherwise result from surrounding blood, debris, and soft tissue filling in the area.

The cannulated tabs 8 at the outer ends 4 of the bridge 2 of the staple 1 aid in the placement of the grooves 5 along the guide wires 7. For example, the proper positioning of the staple 1 can be verified using fluoroscopic images of the guide wires 7 prior to the drilling of holes or inserting the staple 1. The staples 1 can then be placed accurately and there is no need to re-drill the holes to properly insert the staple 1 and repair the bone. The procedure is greatly simplified and expedited, while the outcomes of the surgical procedures are improved as well.

Figures 7, 8:
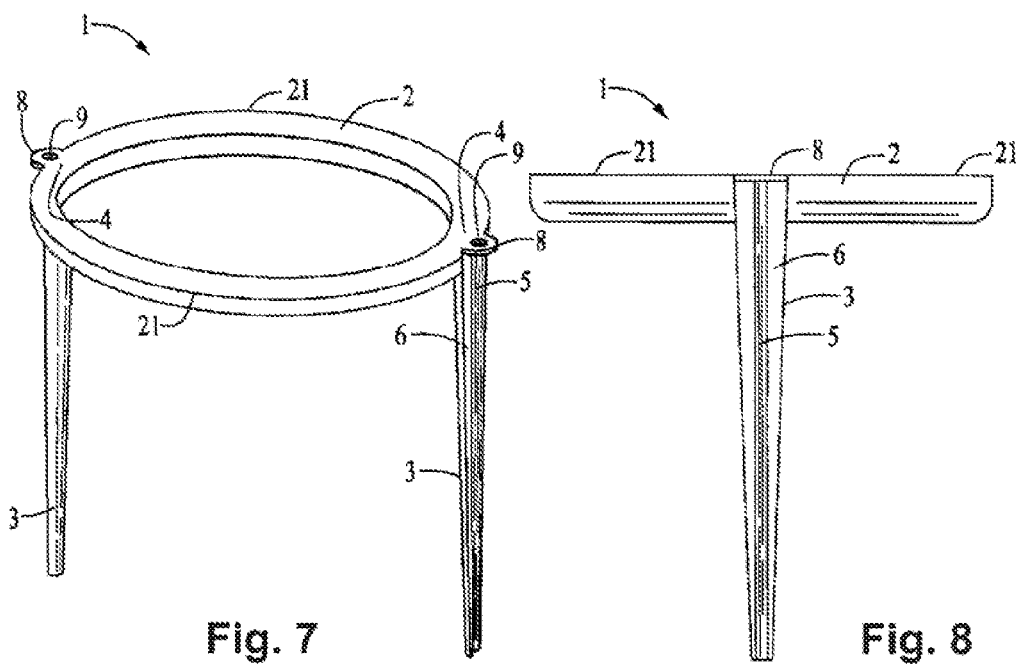
FIG. 7 is a side perspective view of a surgical staple according to the present invention.
FIG. 8 is a side orthogonal view of a surgical staple according to the present invention.
Figure 9:
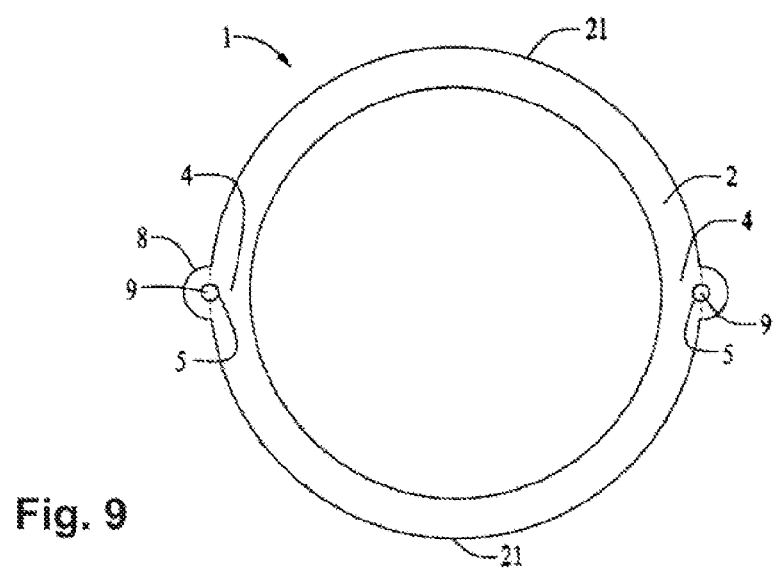
FIG. 9 is a top orthogonal view of a surgical staple according to the present invention.
Figure 13:
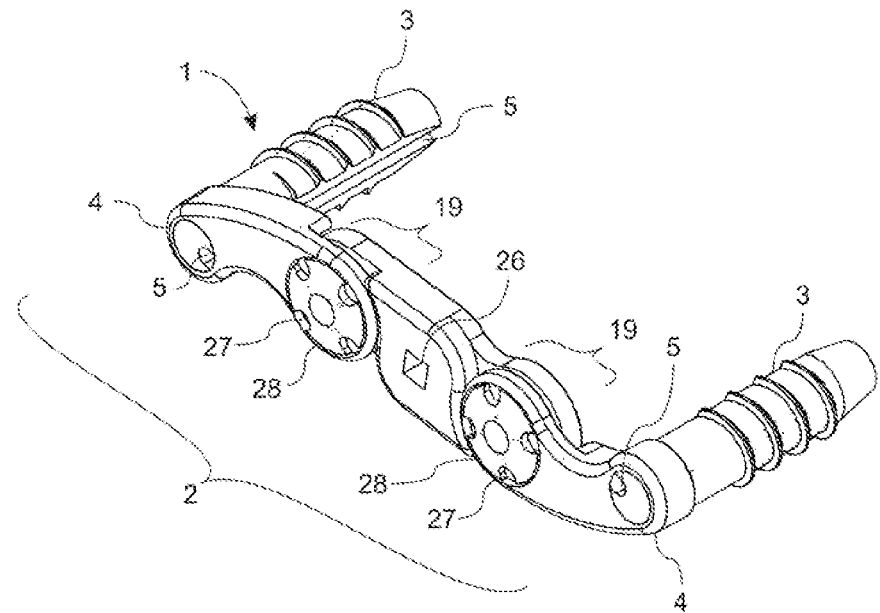
FIG. 13 is a top/side perspective view of a surgical device having two adjustable anti-reversing portions according to the present invention.

Further, the bridge 2 of the staple 1 can be formed in a curved or slight "C" shape. As illustrated in FIGS. 1-5, the staple's bridge 2 is curved to the side so that its axis is substantially perpendicular to the staple's legs 3. In another embodiment, the staple's bridge 2 can be curved upward so that its axis is substantially parallel to the staple's legs 3. In yet another embodiment, the bridge 2 is formed in a substantially circular shape and is perpendicular to the staple's legs, as shown in FIGS. 7-9. In this embodiment, the bridge 2 is comprised of two "C" shaped extensions 21 that converge at the legs 3 of the staple 1.

The staple 1 can provide compression through a variety of means, including via manually compressible staples and staples made from memory metal. Besides aligning the staple 1 for proper placement to accept the guide wires 7, the tabs 8 and apertures 9 therethrough serve an additional helpful function for compression. In the case of manually compressible staples, a device for compressing the staple can be inserted into holes 9 in the tabs 8 and used to bring the legs 3 of the staple 1 together after the staple's insertion. Alternatively, in an embodiment in which the staple 1 is made from memory metal, the staple can be "memoried" in the compressed position with the legs 3 and ends of "C" shaped bridge 2 close together. In this case, the insertion tool can be used to separate the legs 3 from under the bridge 2 and along the grooves 5 located on the inner side of the legs 3, and push the legs 3 outward when activated. The staple 1 is inserted over the guide wires 7 before removing the insertion tool. Removal of the insertion tool will allow the staple 1 to return to its compressed position.

Also, staples made with shape memory alloys can have a memory transfer temperature that is close to body temperature. When the staple is attached with both ends of a broken bone the plate will contract from body heat or applied heat and retain its original shape, thereby exerting a compression force on the broken bone at the place of fracture.

The mechanism of compression can be greatly enhanced by forming the bridge 2 of the staple 1 in a slightly curved or slight "C" shape. For example, when the edges of the "C" are brought together, either by manual compression or the action of memory metal, the legs 3 of the staple 1 in their entirety move toward one another, thereby creating even compression.

With reference to FIG. 5, the staple 1 can include spikes, barbs, or other similar type of projections 11 along the legs 3 of the staple 1. The projections 11 can help stabilize the staple's placement in a bone.

FIGS. 6A-6I illustrate components of a surgical device system and a method for inserting the grooved and tabbed compression staple 1 according to the present invention. The surgical device system for repairing bone according to the present invention comprises grooved and tabbed staples 1 of varying widths and lengths that can be made of various materials; an adjustable width guide device 12; guide wires 7; drills 13 with drill bits of varying diameters; a depth gauge 14; an optional staple insertion/compression device; and an optional tamp or mallet.

Figure 6B:
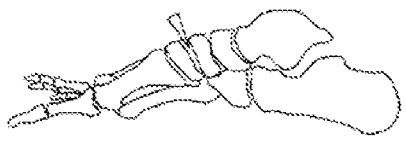
Figure 6C:
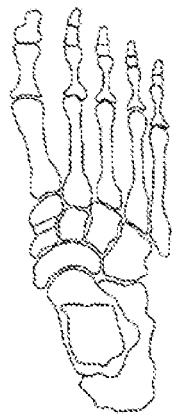
Figure 6D:
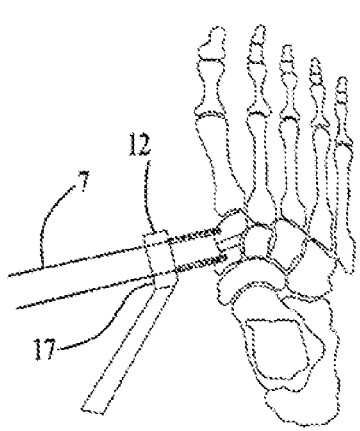

More specifically, as illustrated in FIG. 6D and in FIGS. 10-12, the guide device 12 includes two apertures 17 therethrough and is capable of accepting two guide wires 7 at a desired width across the bone fracture for their insertion. The width between the apertures 17 therethrough, which guides the two guide wires 7, is adjustable so that an appropriate bridge 2 width of the staple 1 can be selected depending on the needs during the surgery. For example, the width between the apertures 17 can be adjusted by slide-type or other mechanism in which the user can select the position, and lock into place, one or both of the apertures 17. As another example, a practitioner can select and lock the width of the guide device 12 itself using a slide-type or other mechanism, which in turn positions the width between the apertures 17.

Alternatively, the apertures 17 of the guide device 12 can be sized to accept and guide a drill 13. In this alternative embodiment, as shown in FIGS. 10-12, removable inserts 18 can be placed in the apertures 17 of the guide device 12. The removable inserts 18 are sized to accept the guide wires 7. The inserts 18 can subsequently be removed so that the guide device 12 can accept a drill 13 over the guide wires 7. Thus, the same guide device 12 can be used to both insert the guide wires 7 in a desired position and to guide a drill 13 with a drill bit that accepts the guide wires 7 to drill holes around the guide wires 7 while the guide device 12 remains in the proper position. This embodiment is useful when it is necessary to use a device to guide the drill, in order to protect soft tissue while drilling.

Figure 6E:
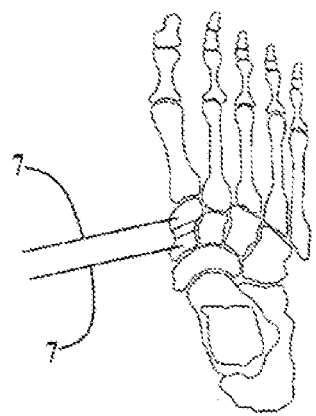
Figure 6F:
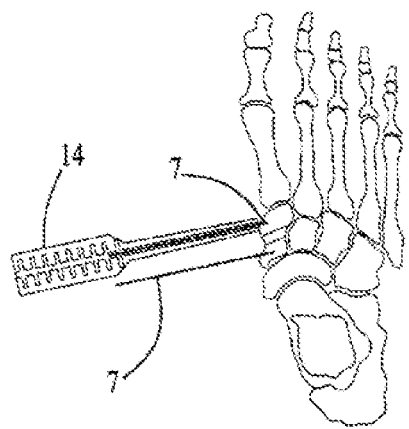

As shown in FIG. 6F, a non-limiting embodiment of the depth gauge 14 can be placed over or along the side of a guide wire 7 of a known length and measure the depth of the wire's insertion at one end of the wire thereof. The difference in the position of the wire 7 in the depth gauge 14 before and after the wire's insertion indicates what length of the staple's legs 3 is appropriate to use. Thus, the depth gauge 14 simplifies measurement of the hole bored in the bone. The depth gauge 14 also determines whether the hole in the bone is at the desired depth. Alternatively, the guide wire 7 itself can have an indicator, such as a ruler-type indicator, that measures and displays the depth of its insertion and therefore determines the appropriate length of the fastener to use. The depth gauge 14 and guide wires 7 can use an electronic or manual means of displaying the depth measurement.

Figure 6G:
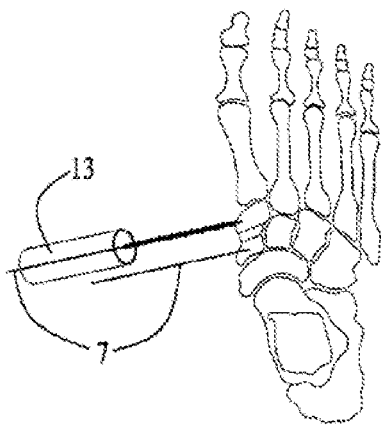

The drill 13 is shown in FIG. 6G, and includes a drill bit having an axially disposed aperture therethrough for accommodating the guide wire 7. Thus, the drill bit can be placed directly above the guide wire 7 and accepts the guide wire 7 through the axially disposed aperture of the drill bit. The drill is lowered toward the bone while surrounding the guide wire 7, and a hole can be drilled directly around the guide wire 7 in the desired area of the bone marked by the guide wire 7. The drill 13 allows for minimal incision conditions so that guide wires 7 stay in place during and after drilling the holes in the bone so that the staple may be inserted directly after the hole is made in the bone around the guide wire 7 without removal of the guide wire 7. As mentioned above, this prevents the problem of losing sight of the drilled holes due to their filling with debris. The drill 13 can use instrumentation that is power-driven or instrumentation that is manipulated manually by hand. The drill 13 can also be used with drill bits of varying diameters.

The following is a non-limiting description of a method of staple insertion. FIG. 6A shows the fractured bone. The fracture, osteotomy or fusion site is exposed, prepared and reduced using standard surgical dissection and reduction techniques as illustrated in FIGS. 6A to 6C. As shown in FIG. 6D, the adjustable guide device 12 is then set at the desired width, which is determined by positioning the guide 12 over the appropriate site. Guide wires 7 are then inserted through the guide device 12 while maintaining the guide in proper position. The guide wires 7 are adapted so that they can be inserted into the bone without requiring a pre-drilled hole prior to their insertion and lodging in the bone. As shown in FIG. 6E, the guide device 12 is removed and the position of the guide wires 7 can be confirmed clinically and fluoroscopically. As shown in FIG. 6F, a depth gauge 14 is used to assess the appropriate length of the staple's legs 3 by measuring the exposed length of the wire 7.

Figure 6H:
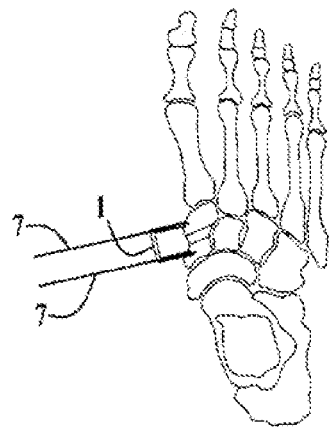
Figure 6I:
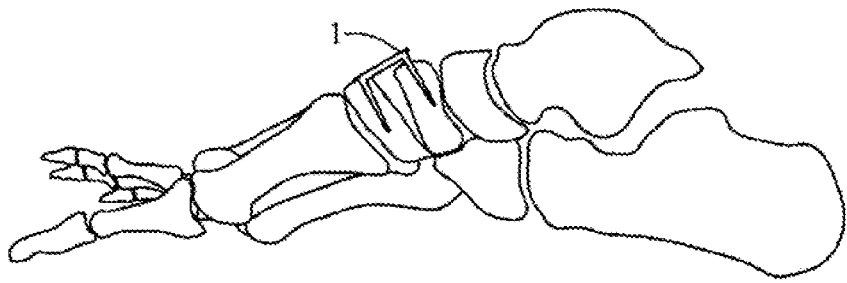

To seat the staple 1, holes will then be drilled around the guide wires 7 and into the bone using the drill 13 as described above, and as shown in FIG. 6G. As shown in FIGS. 6H and 6I, the appropriate sized tabbed and grooved staple 1 is aligned with the guide wires 7 and inserted into the bone. The guide wires 7 are subsequently removed. The compressing feature of the staple 1 can be activated automatically, manually or by the use of heat as needed, as described above. A tamp or mallet can be used as needed to further seat the staple. Final fluoroscopic images can be obtained to confirm placement and reduction before flushing and closing in the typical manner known in the art.

An alternative method for using a system in which the guide device 12 includes removable inserts 18 within the apertures 17 of the guide device 12 is also disclosed. According to a method using this guide device 12, both the guide wires 7 and the drill 13 can be guided into the bone using the guide device 12. A user can place the guide device 12 in a desired position over a bone fracture and then select the desired position or width between the apertures 17. Guide wires 7 can be inserted through the inserts 18 of the apertures 17 and into bone fragments. Once the guide wires 7 are in place, the inserts 18 can be removed. The user can then drill around the guide wires 7 and through the apertures 17 of the guide device 12 with a drill 13 as described above. After drilling, the guide device 12 is removed and a surgical staple 1 can be aligned with and guided by the guide wires 7 and inserted into the drilled holes in the bone. The guide wires 7 can be removed, and the staple 1 can be compressed and seated. As with the previous method, the positions of the guide wires 7 and the staple 1 can be confirmed fluoroscopically.

In another embodiment, the surgical device 1 described herein comprises a bridge 2 having one or more adjustable anti-reversing portions 19. The device 1 further comprises two or more attached or detached legs 3. The adjustable anti-reversing portion(s) 19 enable the device 1 to provide fixation or distraction of one body part relative to another body part, including such body parts as tissues, bones, and fragments thereof. For example, a practitioner can surgically implant the legs of the device 1 having adjustable anti-reversing portion(s) 19 into a first and second body part. Once inserted, the practitioner can adjust the adjustable anti-reversing portion(s) 19 to bring the first and second body parts either together for fixation or apart for distraction. The adjustable anti-reversing portion(s) 19 can also be adjusted prior to insertion if needed.

Figure 14:
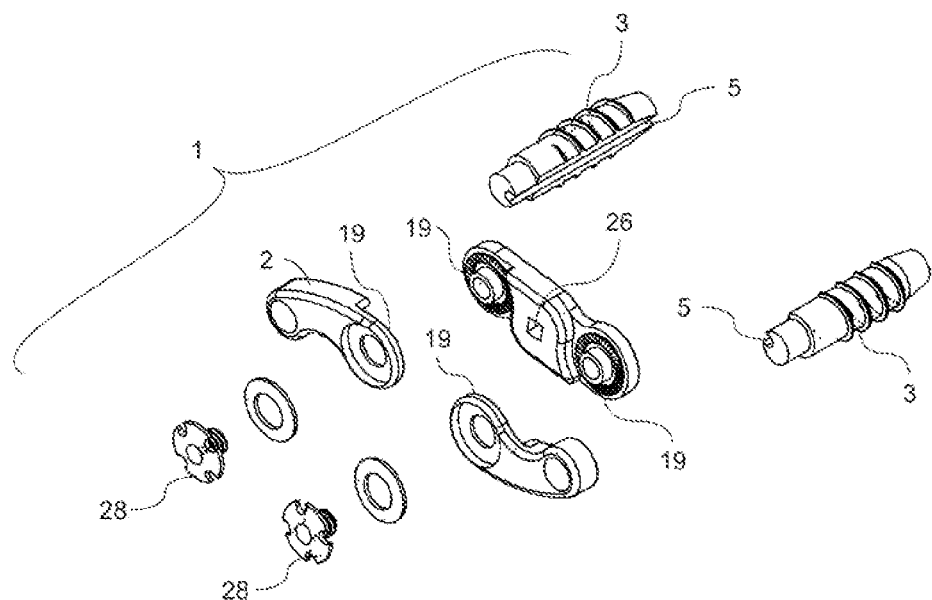
FIG. 14 is an exploded view of a surgical device having two adjustable anti-reversing portions according to the present invention.
Figure 15:
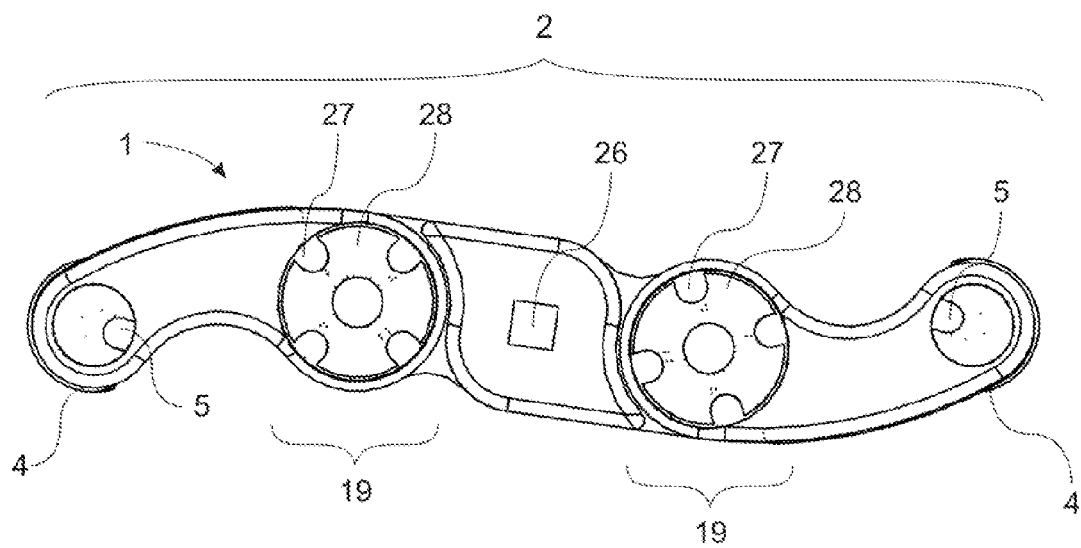
FIG. 15 is a top orthogonal view of a surgical device having two adjustable anti-reversing portions according to the present invention.
Figure 16:
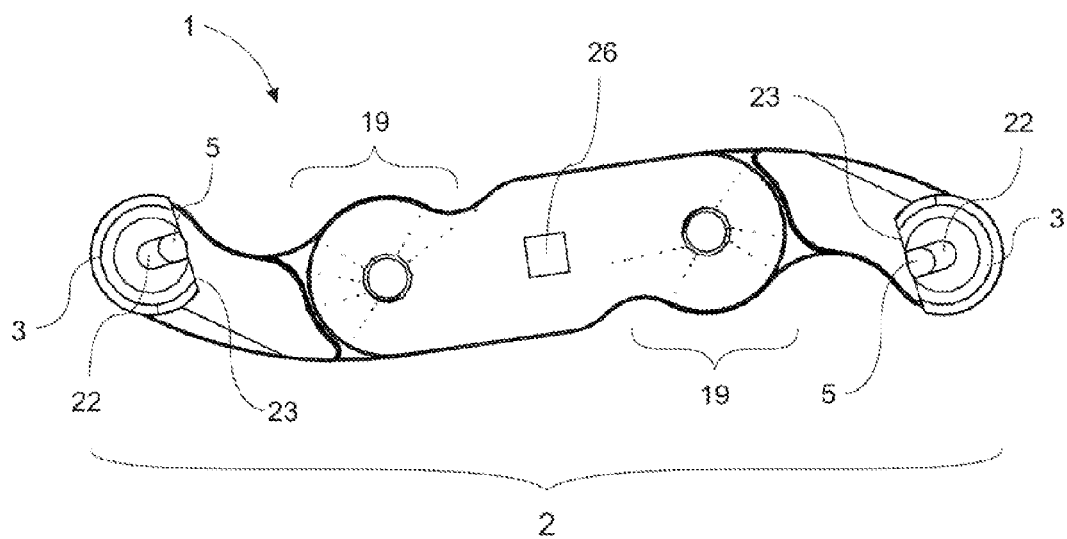
FIG. 16 is a bottom orthogonal view of a surgical device having two adjustable anti-reversing portions according to the present invention.
Figure 17:
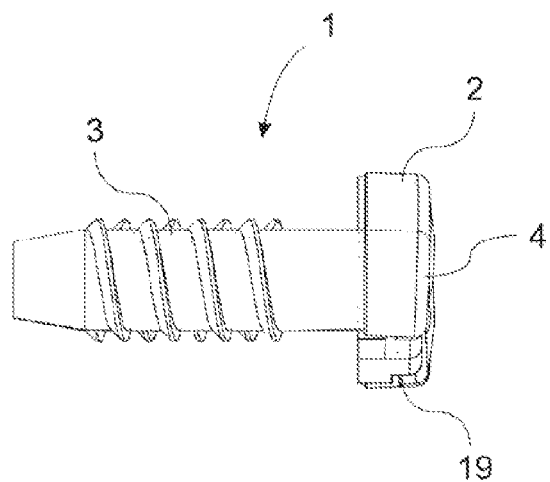
FIG. 17 is a side orthogonal view of a surgical device having adjustable anti-reversing two portions according to the present invention.
Figure 18:
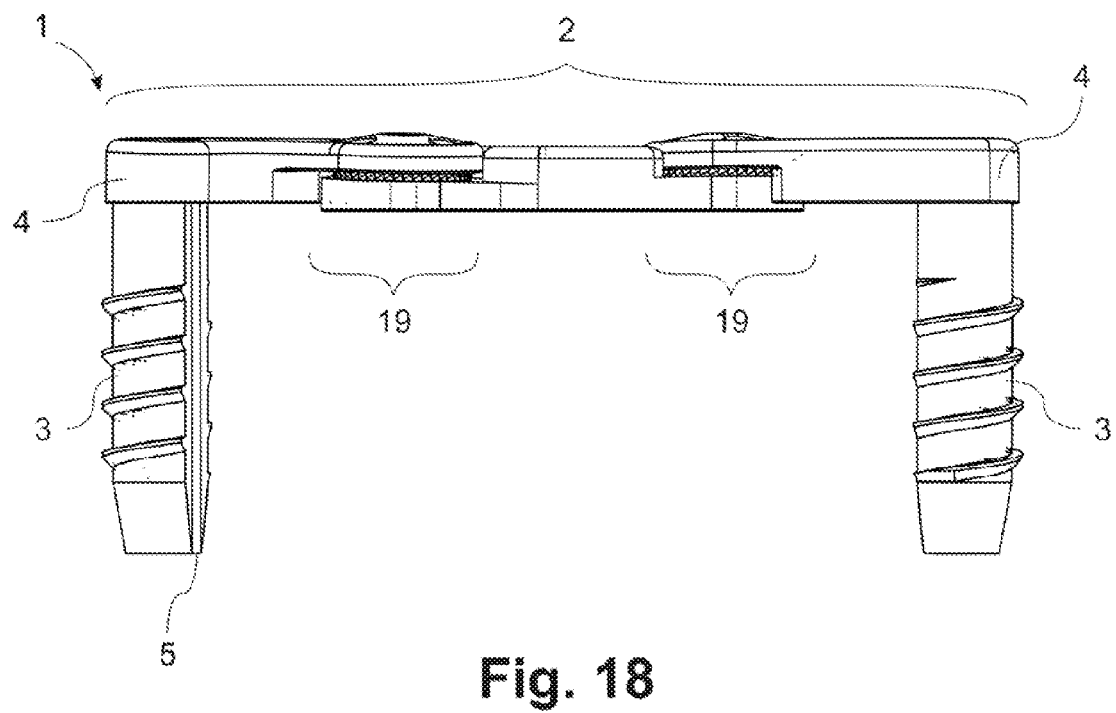
FIG. 18 is a front perspective view of a surgical device having two adjustable anti-reversing portions according to the present invention.
Figure 19:
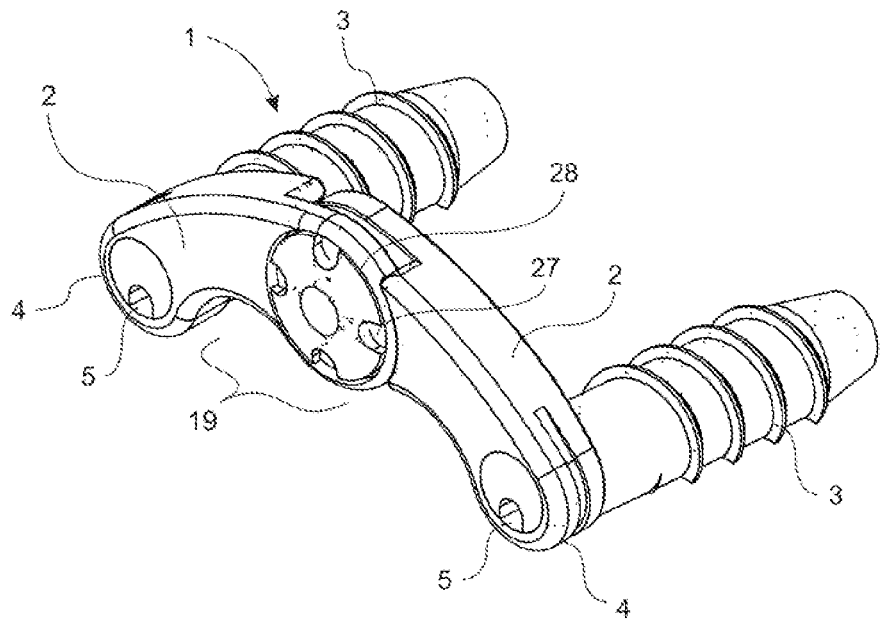
FIG. 19 is a top/side perspective view of a surgical device having one symmetrically-positioned adjustable anti-reversing portion according to the present invention.
Figure 20:
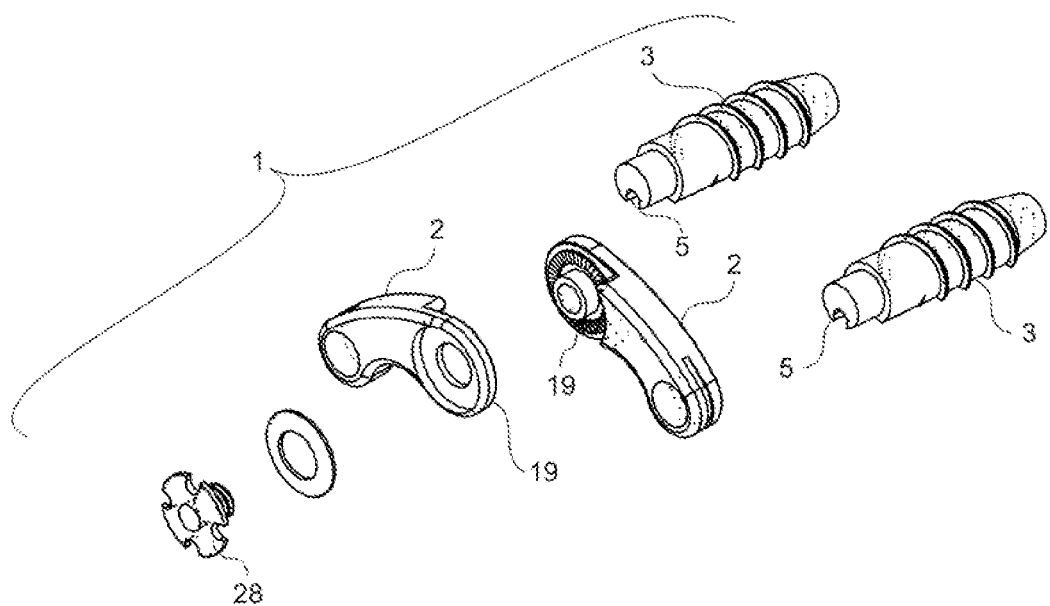
FIG. 20 is an exploded view of a surgical device having one symmetrically-positioned adjustable anti-reversing portion according to the present invention.
Figure 28:
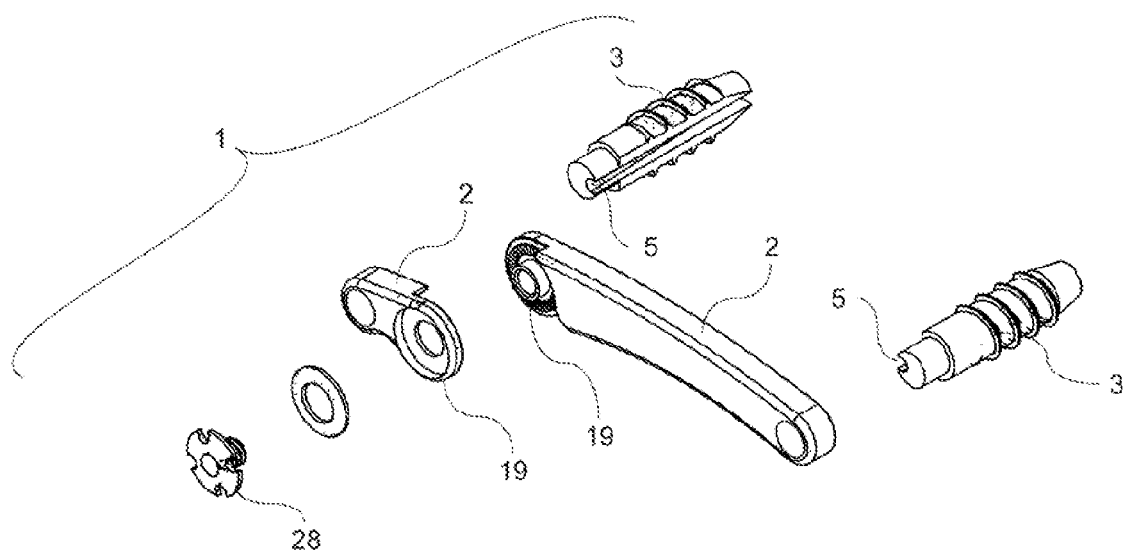
FIG. 28 is an exploded view of a surgical device having one asymmetrically-positioned adjustable anti-reversing portion according to the present invention.
Figure 29:
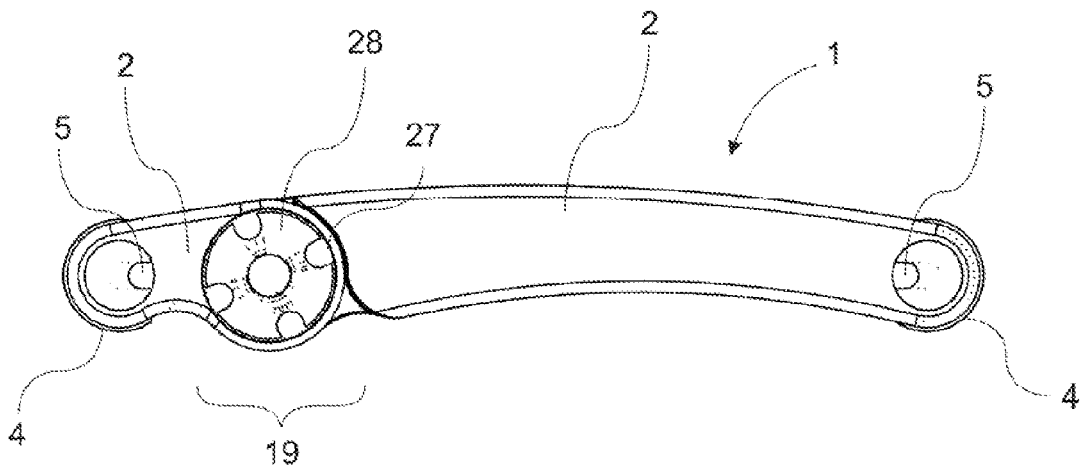
FIG. 29 is a top orthogonal view of a surgical device having one asymmetrically-positioned adjustable anti-reversing portion according to the present invention.
Figure 30:
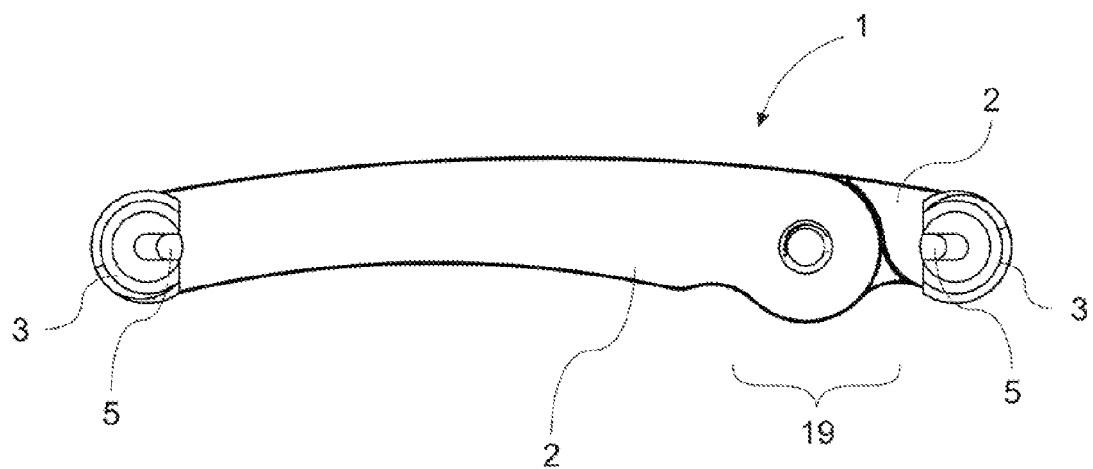
FIG. 30 is a bottom orthogonal view of a surgical device having one asymmetrically-positioned adjustable anti-reversing portion according to the present invention.
Figure 31:
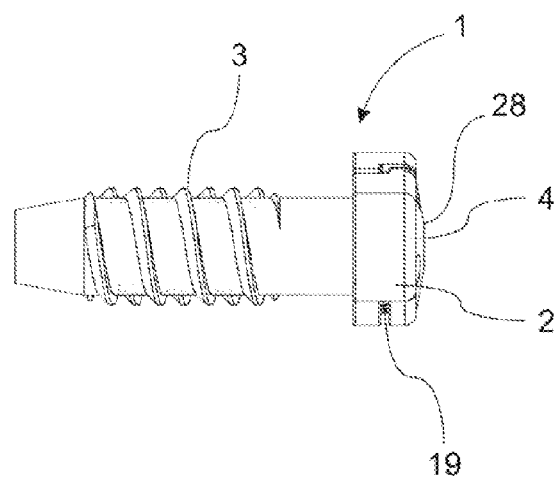
FIG. 31 is a side perspective view of a surgical device having one asymmetrically-positioned adjustable anti-reversing portion according to the present invention.
Figure 32:
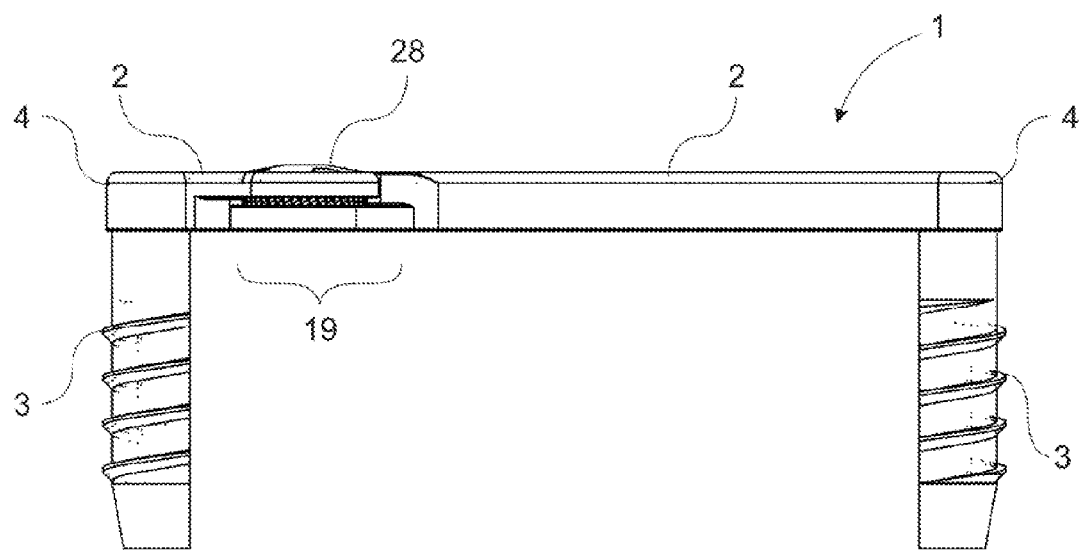
FIG. 32 is a front perspective view of a surgical device having one asymmetrically-positioned adjustable anti-reversing portion according to the present invention.
Figure 33:
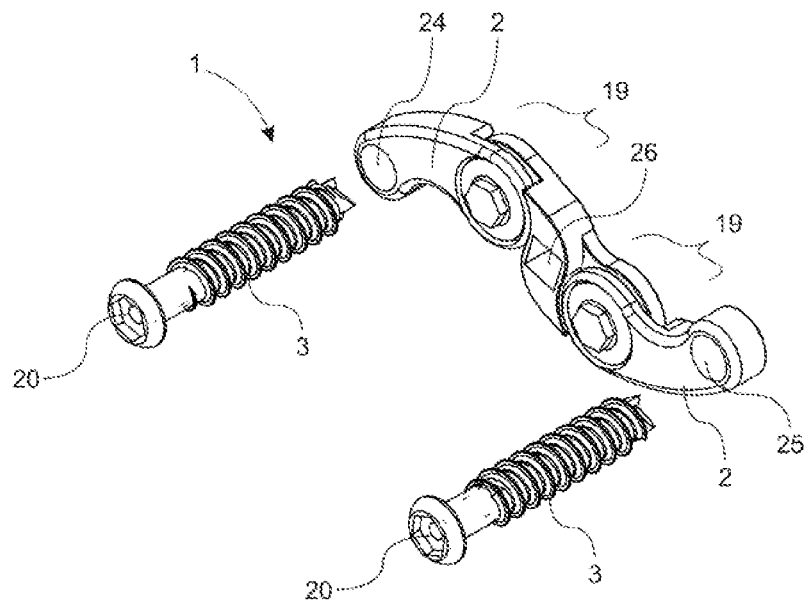
FIG. 33 is a top side perspective view of a surgical device having at least one adjustable anti-reversing portion, two apertures, and detached legs according to the present invention.
Figure 34:
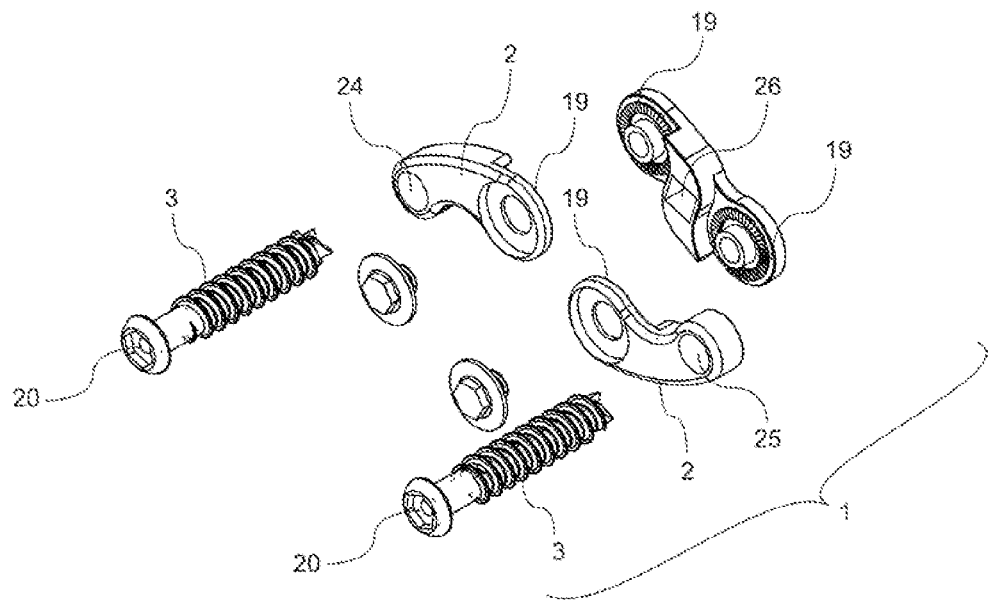
FIG. 34 is an exploded view of a surgical device having at least one adjustable anti-reversing portion, two apertures, and detached legs according to the present invention.
Figure 35:
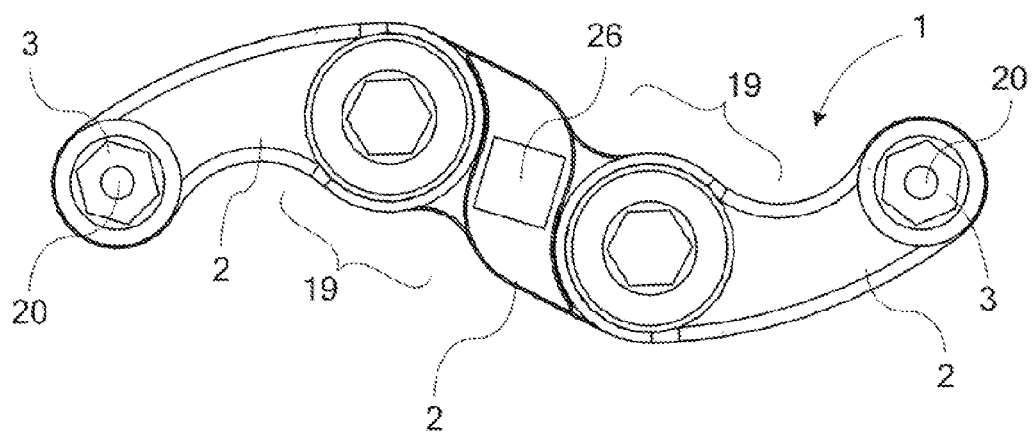
FIG. 35 is a top orthogonal view of a surgical device having at least one adjustable anti-reversing portion, two apertures, and detached legs according to the present invention.
Figure 36:
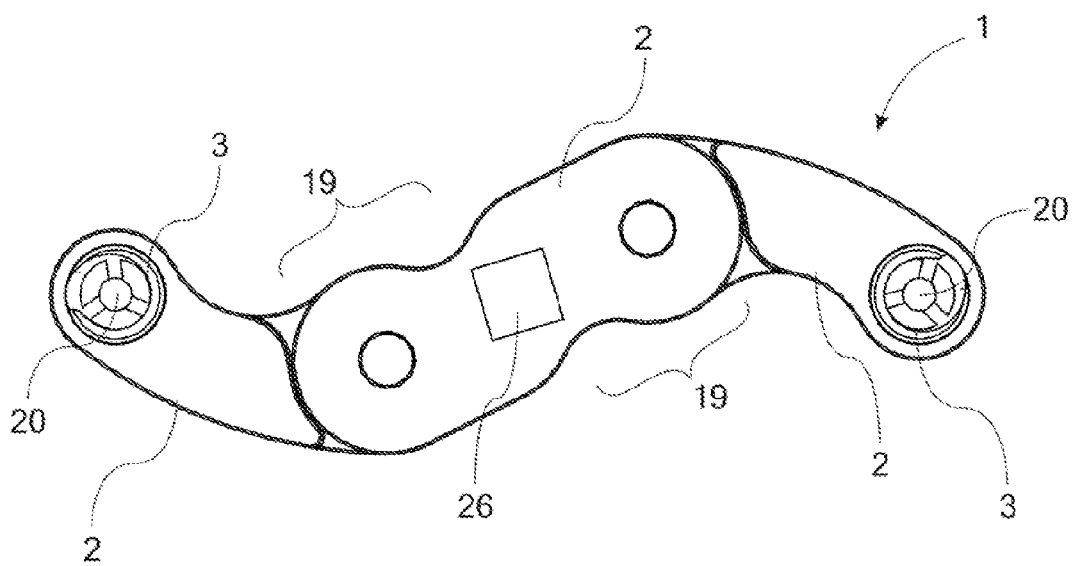
FIG. 36 is a bottom orthogonal view of a surgical device having at least one adjustable anti-reversing portion, two apertures, and detached legs according to the present invention.
Figure 37:
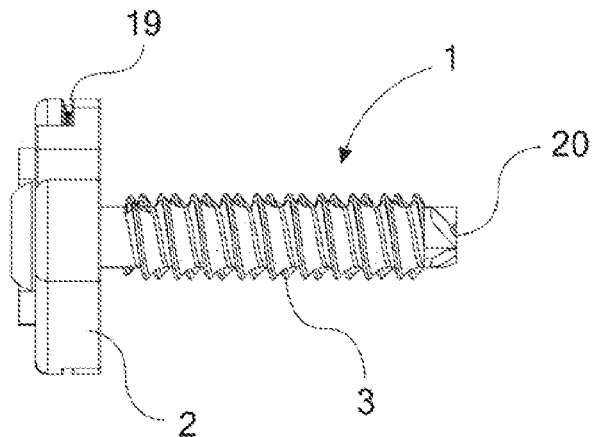
FIG. 37 is a side perspective view of a surgical device having at least one adjustable anti-reversing portion, two apertures, and detached legs according to the present invention.
Figure 38:
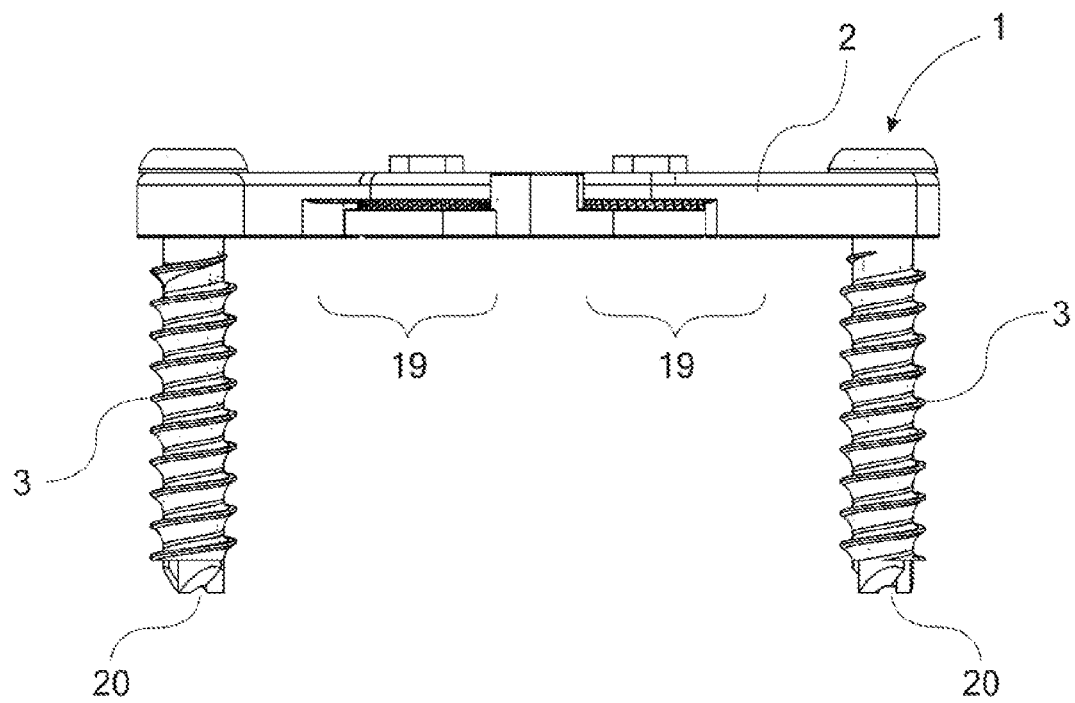
FIG. 38 is a front perspective view of a surgical device having at least one adjustable anti-reversing portion, two apertures, and detached legs according to the present invention.

Several views of the embodiment of the device 1 having a bridge 2 with one or more adjustable anti-reversing portions 19 are shown in FIGS. 13-47. More specifically, FIGS. 13-18, and 33-38 illustrate several views of an embodiment of the device 1 including two adjustable anti-reversing portions 19. FIGS. 19-26 and 46A-47C show several views of an embodiment of the device 1 having one adjustable anti-reversing portion 19 integrated with the bridge 2 of the device 1 and positioned symmetrically between the device's legs 3. FIGS. 27-32 show several views of an embodiment of the device 1 having one adjustable anti-reversing portion 19 integrated with the bridge 2 of the device 1 and positioned asymmetrically between the device's legs 3. Exploded views of these three embodiments are shown in FIGS. 14, 20, and 28.

The device 1 is not limited to such illustrated embodiments; the device 1 can integrate one or more adjustable anti-reversing portion(s) 19 in any position along the bridge 2 of the device 1. As described herein, the device's legs 3 can be solid, e.g., bone screws, cannulated, or grooved. The legs 3 can be permanently attached with, or integrated with, the device's bridge, as shown in FIGS. 13-32. The legs 3 can also be detached and separate from the device's bridge 2, as shown in FIGS. 33-38. When the legs 3 of the device 1 are permanently integrated with the bridge 2, or detached legs 3 are assembled with the bridge, the device 1 resembles a surgical staple. The device can also be described as an adjustable plating system, wherein the bridge with adjustable anti-reversing portion(s) 19 of the device 1 resembles an adjustable bone plate that can be assembled with the detached legs 3, such as bone screws. Further, the device 1 can utilize two or more attached legs 3, two or more detached legs 3, or a combination of two or more attached and detached legs 3.

As described above, the device 1 need not have the device's legs 3 fixed or permanently attached to the bridge 2. The device's legs 3 can be separate from the bridge 2, e.g., bone screws, and subsequently attached with the bridge 2 upon insertion into bone or tissue, as described below. As shown in FIGS. 33-38, the device 1 has detached legs 3 and a bridge 2 that comprises a first aperture 24 and a second aperture 25 therethough. The bridge further comprises at least one adjustable anti-reversing portion(s) 19 located in between the first aperture 24 and second aperture 25. In the embodiment shown in several views in FIGS. 33-38, the device having a bridge 2 with detached legs 3 includes two adjustable anti-reversing portions 19. The device 1 having detached legs 3 can also include only one symmetrically positioned adjustable anti-reversing portion 19 or one asymmetrically positioned adjustable anti-reversing portion 19, as shown in the previous embodiments of the device 1 with attached legs 3.

In the embodiment of a device 1 with detached legs 3 and a bridge having a first aperture 24 and second aperture 25 therethrough, the device's legs 3, such as bone screws, can be inserted through the first 24 and second apertures 25 and into bone or tissue to thereby form a device 1 with legs 3 upon the device's insertion. Like the embodiment of the device 1 having adjustable anti-reversing portion(s) 19 and permanently attached legs 3, the legs 3 of the embodiment of the device 1 having detachable legs 3 can be solid, e.g., bone screws, cannulated, or grooved. The bridge 2 of the device 1 can include more than two apertures to accommodate an embodiment of the device 1 having more than two legs 3, if desired.

While FIGS. 13-44 illustrate the embodiments of the surgical device 1 with adjustable anti-reversing portion(s) 19 as having cannulated or grooved device legs 3, the device 1 can also have solid legs 3 that can be surgically implanted using standard surgical techniques. The device 1 including adjustable anti-reversing portion(s) 19 can also incorporate the aforementioned features of the embodiment of the surgical device 1 without adjustable anti-reversing portions that is described herein. For example, the legs 3 of the device 1 can substantially solid and have at least two elevations, an inner elevation 22 and an outer elevation 23, that run down the length of each device leg 3. The inner elevation 22 can be defined as the inner most surface of the leg 3. The outer elevation 23 can be defined as the outer most surface of the leg 3.

Figure 21:
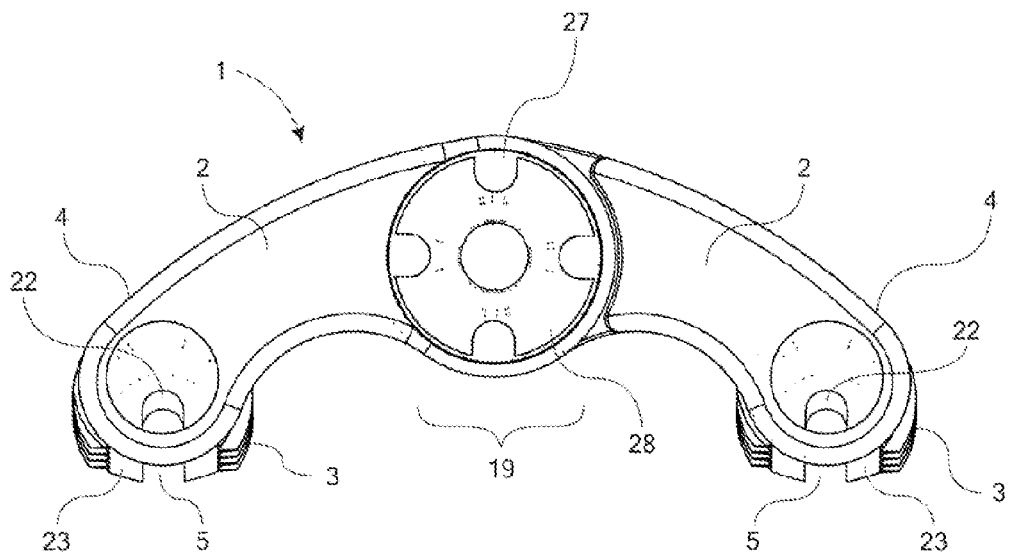
FIG. 21 is a top perspective view of a surgical device having one symmetrically-positioned adjustable anti-reversing portion according to the present invention.
Figure 22:
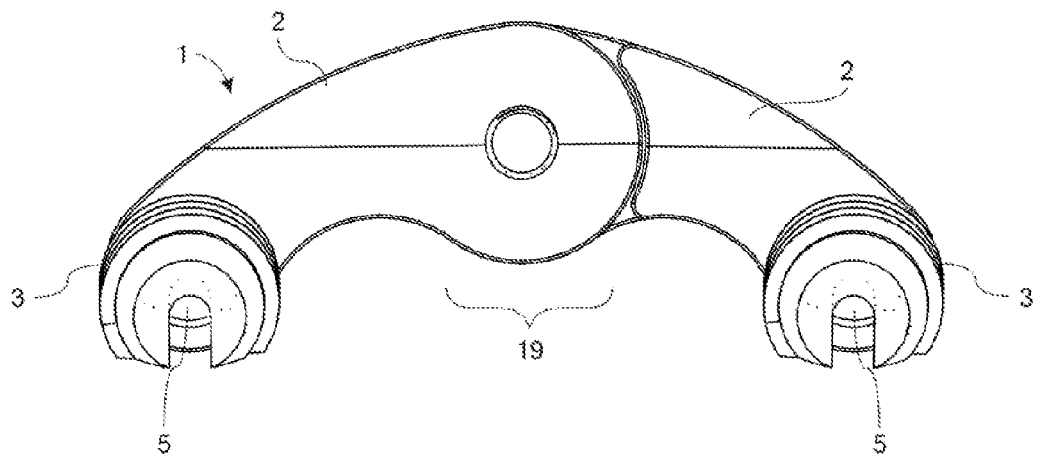
FIG. 22 is a bottom perspective view of a surgical device having one symmetrically-positioned adjustable anti-reversing portion according to the present invention.
Figure 23:
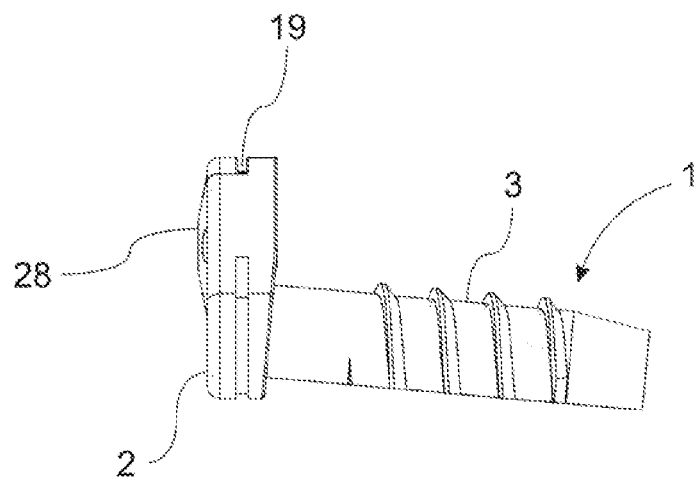
FIG. 23 is a right side perspective view of a surgical device having one symmetrically-positioned adjustable anti-reversing portion according to the present invention.
Figure 24:
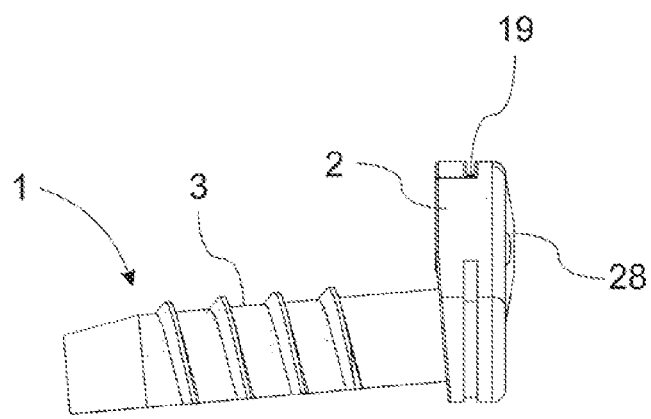
FIG. 24 is a left side perspective view of a surgical device having one symmetrically-positioned adjustable anti-reversing portion according to the present invention.
Figure 25:
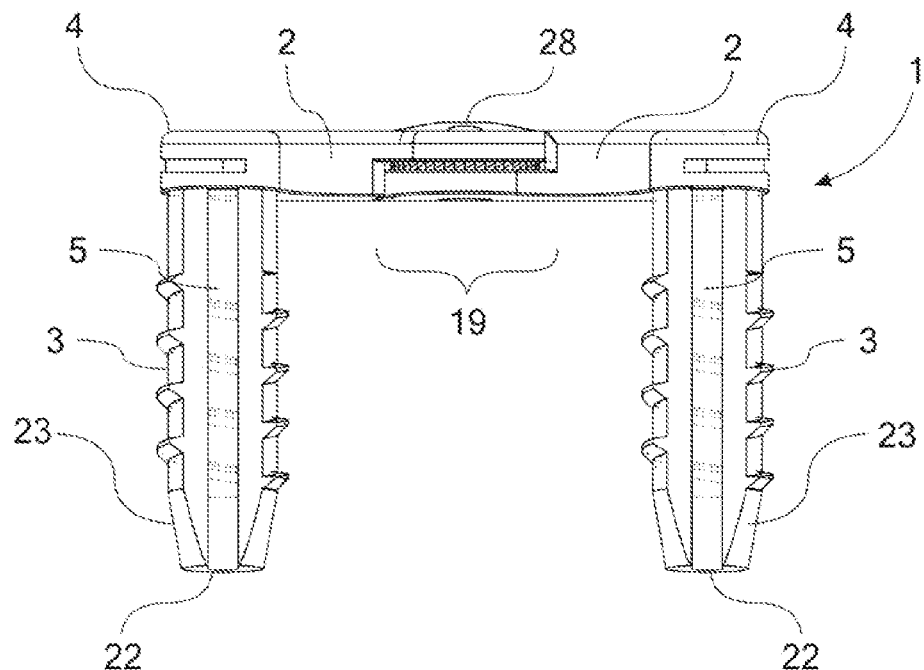
FIG. 25 is a front perspective view of a surgical device having one symmetrically-positioned adjustable anti-reversing portion according to the present invention.
Figure 26:
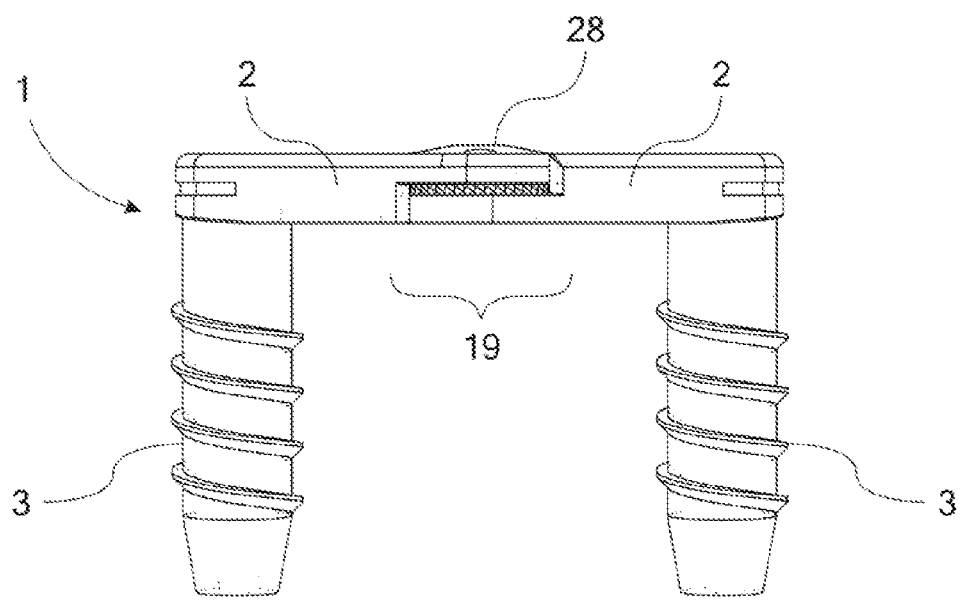
FIG. 26 is a back perspective view of a surgical device having one symmetrically-positioned adjustable anti-reversing portion according to the present invention.
Figure 27:
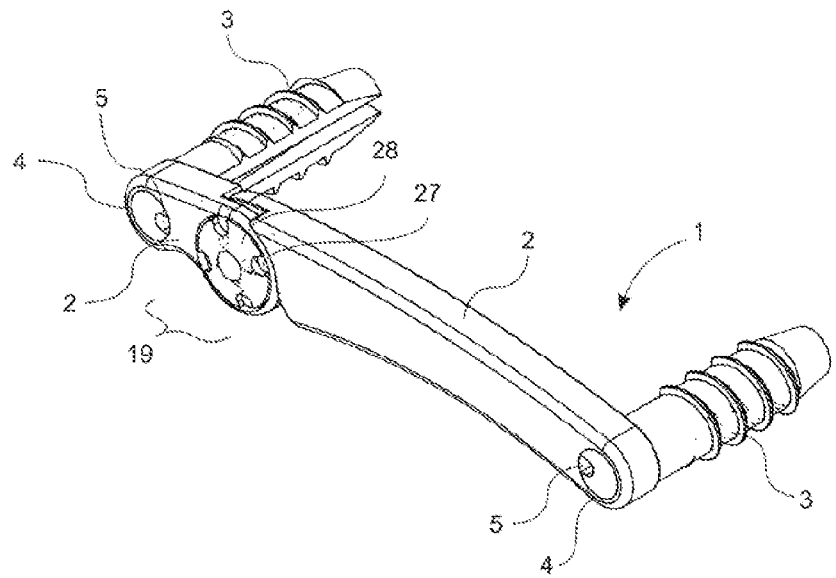
FIG. 27 is a top side perspective view of a surgical device having one asymmetrically-positioned adjustable anti-reversing portion according to the present invention.

As shown in FIGS. 21 and 25, the inner elevation 22 and outer elevation 23 can form U-shaped grooves 5 that run down the entire length of each device leg 3, however, it is not necessary that a U-shaped groove be formed nor that the grooves 5 be formed along the entire length of each device leg 3. The inner elevation 22 and outer elevation 23 can also form an L-shaped groove 5 along the length of each device leg 3 (not shown). In the embodiment with attached device legs 3, the bridge-to-leg interface 4 can be solid, therefore the device 1 avoids any problems of weakness or breakage in the device's legs 3 or bridge-to-leg interface 4 that hollow or cannulated device legs can create. The legs 3 of the device 1 can be tapered or not tapered towards the ends of the legs 3 that are distal from the bridge 2. Also, the distal ends of legs 3 of the device can be blunt or formed to an acute point.

The grooves 5 can run down any edge of each of the legs 3, such as the front, back, inner or outer edges of the legs 3. As shown in FIGS. 13-18 and 27-32, the grooves 5 run down the inner edge of the legs 3. As shown in FIGS. 19-26, the grooves 5 run down the front edge of the legs 3. The grooves 5 can also be described as a recess. The function of the groove 5 is served so long as the leg 3 has at least two elevations relative to the central axis of the leg. As shown in FIGS. 33-38, the device 1 can also utilize cannulated legs 3 comprising an aperture 20 extending axially through each device leg. The grooved or cannulated legs can accept guide wires 7 therethrough to guide the device's insertion during a surgical procedure. In the alternative, the legs 3 of each of the device's embodiments can be solid.

The adjustable anti-reversing portion(s) 19 of the bridge can comprise any anti-reversing mechanism, including, but not limited to, a hinged system, a one-way sliding track system, a ratchet system, such as a gear and pawl system, a rack and pinion system, and a one-way clutch system. For example, as shown in FIGS. 13-38, a hinged or ratchet system can include a round gear with a first set of teeth, and a second round gear with a second set of teeth or a pawl that engages the first set of teeth. The first set of teeth are uniform but asymmetrical, with each tooth having a moderate slope on one side and a much steeper slope on the other side. When the teeth are moving in the unrestricted direction, the second set of teeth or pawl easily slides up and over the gently sloped sides of the first set of teeth. When the first set of teeth attempt to move in the opposite direction, the second set of teeth or pawl will catch against the steeply sloped side of the first set of teeth, thereby locking it against the teeth and preventing any further motion in that direction. Thus, the adjustable anti-reversing portion(s) 19 allow for continuous rotary motion in only one direction while preventing motion in the opposite direction. The anti-reversing mechanism of the adjustable anti-reversing portion(s) 19 allows for adjusting the adjustable anti-reversing portion(s) at incremental amounts of distance and auto-locking the device 1 in a desired position for compression or distraction.

Figure 47A:
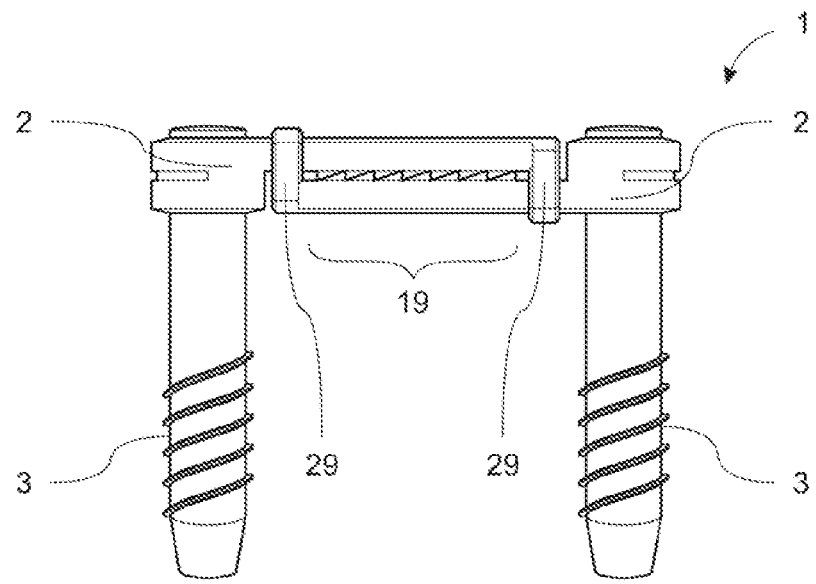
FIGS. 47A-47C are front orthogonal views of a surgical device having an adjustable anti-reversing portion according to the present invention.
Figure 47B:
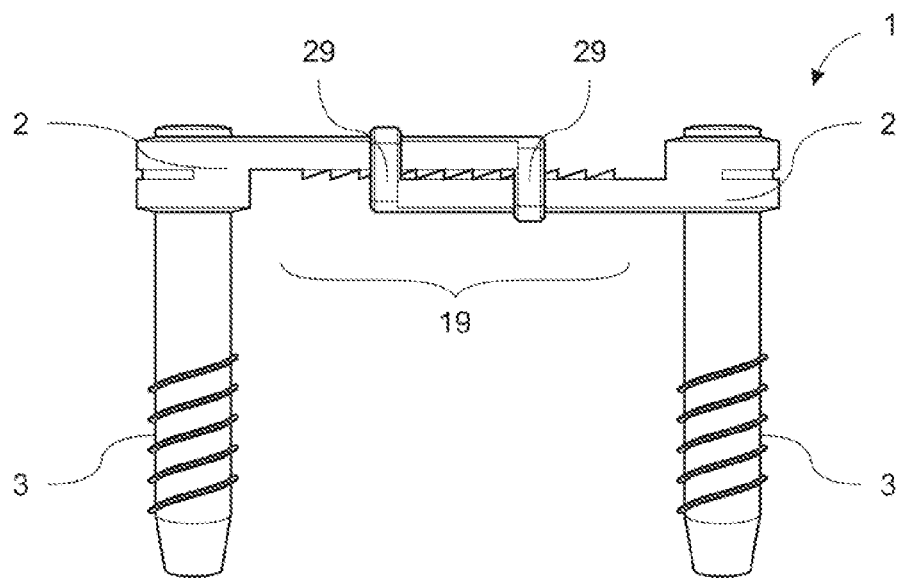
Figure 47C:
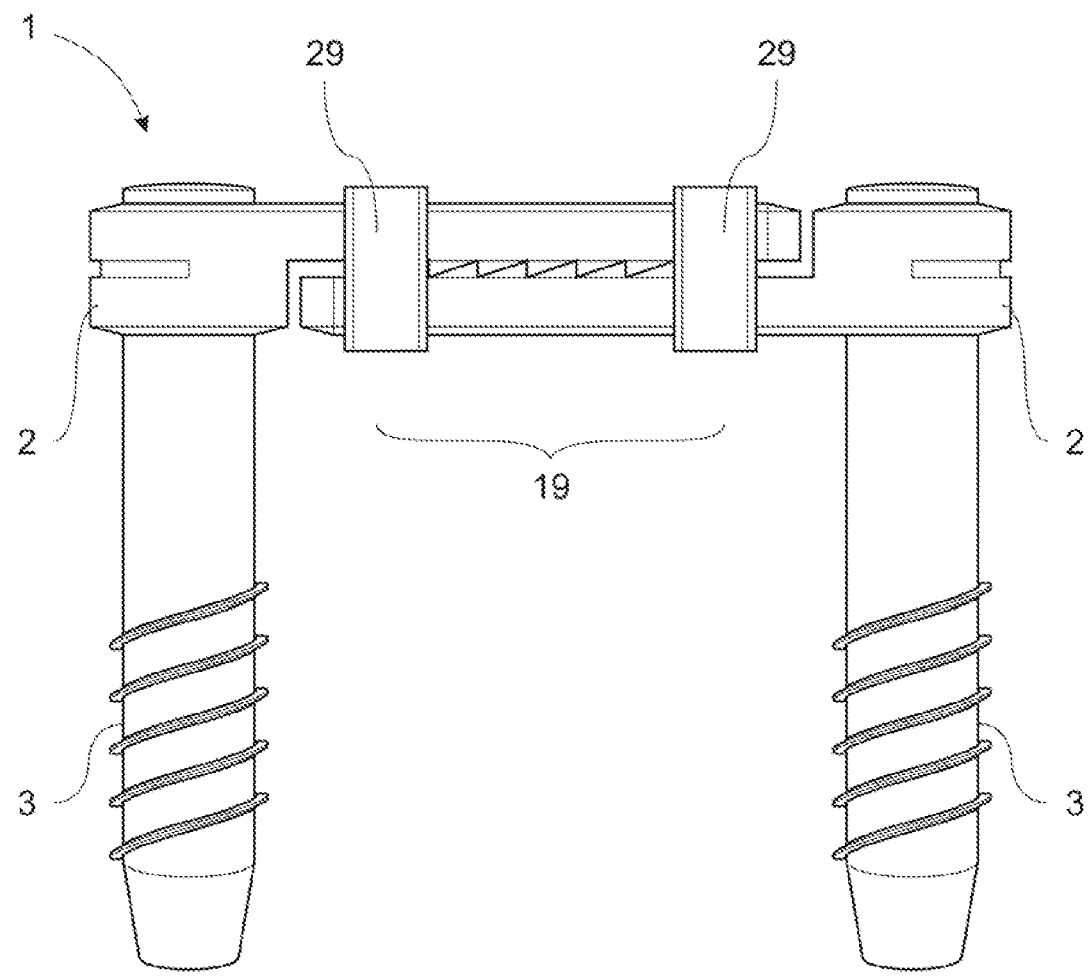

In the alternative to providing anti-reversing or auto-locking movement of the bridge 2 in a rotational manner, the device's adjustable anti-reversing portion(s) 19 can provide anti-reversing or auto-locking movement in a linear direction, e.g., the adjustable anti-reversing portion(s) 19 can slide and lock linearly on a one-way track. As a non-limiting example, FIGS. 47A-47C illustrate a device having an adjustable anti-reversing portion 19 comprising a one-way sliding track system. Like the rotating adjustable anti-reversing portion, the sliding adjustable anti-reversing portion 19 can include teeth that are uniform but asymmetrical, with each tooth having a moderate slope on one edge and a much steeper slope on the other edge, so that the bridge 2 will automatically lock as it slides incrementally over the teeth. Each adjustable anti-reversing portion 19 can be designed to lock the device 1 in a one-way direction to provide compression or lock the device 1 in a one-way direction to provide distraction.

The device 1 of this embodiment can include more than one bridge portions 2 and at least one connecting element 29 to allow the bridge 2 to compress and distract in a linear direction. The connecting element(s) 29 can be comprised of band-like portions that wrap around the bridge 2. As shown in FIGS. 47A and 47B, the connecting element(s) 29 can be integrated in the bridge 2 of the device 1. As shown in FIG. 47C, the connecting element(s) 29 can be separate from the bridge 2, such as separate band(s) that wrap around the bridge 2 of the device 1. The integrated or separate connecting element(s) 29 can be made of the same or different material as that of the device 1.

The user can manually adjust or rotate the adjustable anti-reversing portion(s) 19 to position the device's bridge in a desired angle and provide compression or distraction. Once the user adjusts the adjustable anti-reversing portion(s) 19, the adjustable anti-reversing portion(s) 19 automatically lock in place to resist reversing during compression of the device 1. The adjustable anti-reversing portion(s) 19 of the device 1 can be designed to move in a one-way direction to provide and maintain compression or a one-way direction to provide and maintain distraction. The prior art does not disclose adjustable anti-reversing portion(s) 19 on a device's bridge 2 using an anti-reversing integral ratcheting compression system.

Because the bridge 2 can include more than one adjustable anti-reversing portion(s) 19, the device's legs 3 can be altered independently in more than one direction. Thus, the device 1 can provide both compression and distraction between body parts. The adjustable anti-reversing portion(s) 19 allow for positioning of the legs 3 based on the angles in which the bridge 2 is positioned, utilizing the full 360-degree coplanar range of the device's bridge 2. The prior art does not disclose devices that have legs 3 which can be independently positioned along any angle coplanar to the device's bridge 2.

The adjustable anti-reversing portion(s) 19 can be adjusted prior to insertion of the device 1 into bone or tissue to angle the bridge 2, after insertion to provide compression or distraction, or both before and after surgical insertion of the device 1. For example, prior to the device's surgical insertion, the practitioner can adjust the angle of the adjustable anti-reversing portion(s) 19 of the device's bridge 2 to better align the device's legs 3 with bone fragments that are angled in various positions.

As another non-limiting example, after the device's surgical insertion, the practitioner can adjust the adjustable anti-reversing portion(s) 19 to move the device's legs 3 in closer proximity to one another for improved and maintained compression over staples known in the prior art. Illustrated examples of using the device 1 with adjustable anti-reversing portion(s) 19 in a manner to provide compression are shown in FIGS. 39A-D, 40A-C, and 41A-C. Alternatively, the practitioner can adjust the adjustable anti-reversing portion(s) 19 to move the device's legs 3 farther apart from one another to provide distraction, e.g., maintain separation of an osteotomy for bone re-alignment. An illustrated example of using the device 1 with adjustable anti-reversing portion(s) 19 in a manner to provide distraction is shown in FIGS. 42A-42D. All embodiments of the device 1, e.g., the device 1 with two adjustable anti-reversing portions 19, the device 1 with one symmetrically positioned adjustable anti-reversing portion 19, and the device 1 with one asymmetrically positioned adjustable anti-reversing portion 19, can be designed to lock in an anti-reverse mechanism for compression purposes or designed to lock for in an anti-reverse mechanism for distraction purposes. Moreover, the embodiment having two adjustable anti-reversing portions 19 can be designed such that one adjustable anti-reversing portion 19 can lock in an anti-reversing direction for compression and the other adjustable anti-reversing portion 19 can lock in an anti-reversing direction for distraction.

The user can adjust or rotate the adjustable anti-reversing portion(s) 19 by manually pushing or pulling the bridge 2 or device's legs 3 in the desired inward or outward direction, depending on whether the device's adjustable anti-reversing portion(s) 19 are designed for compression or distraction. The user can also adjust or rotate the adjustable anti-reversing portion(s) 19 by using an instrument that fits into a corresponding aperture(s) 26 in the device's bridge 2 or into a corresponding aperture(s) 27 in the device's adjustable anti-reversing portion(s) 19. The user can also directly manually adjust or rotate adjustable anti-reversion portion (19) itself.

An example of inserting the device 1 into bone and adjusting the adjustable anti-reversing portion(s) 19 with an instrument is shown in FIGS. 39A-D. In particular, insertion of the device 1 having two adjustable anti-reversing portions 19 is shown. As shown in FIG. 39A, the practitioner can drill holes into the bone for the device's insertion with or without the use of guide wires 7. Also with or without the use of guide wires 7, the device is then inserted into the pre-drilled holes, as illustrated in FIG. 39B. The device having two adjustable anti-reversing portions 19 can include an aperture 26 in the bridge 2 between the two adjustable anti-reversing portions 19. As shown in FIGS. 39C-39D, the user can insert an instrument that is designed to fit the aperture 26 between the two adjustable anti-reversing portions 19, turn the instrument in a direction to rotate the adjustable anti-reversing portions 19 to bring the device's legs 3 in closer proximity to one another, and thereby bring the bone fragments together for compression and fixation. The device 1 can also be designed so that the adjustable anti-reversing portions 19 rotate in an opposite direction to move the device's legs 3 farther apart for distraction of bone fragments.

The embodiment of the device having detached device legs 3 can also be inserted in the manner illustrated in FIGS. 39A-D. For example, the practitioner can align the bridge 2 of the device 1 over the predrilled holes in the bone with or without the use of guide wires 7. The practitioner can then insert the device's legs 3 through the first 24 and second apertures 25 in the bridge 2 and subsequently into the bone. Once the device's legs 3 are inserted into the bone, the practitioner can then insert an instrument into the aperture 26 between the adjustable anti-reversing portions to rotate the adjustable anti-reversing portions 19 and thereby bring both the device's legs 3 together for compression and the bone fragments together for compression. Again, in this embodiment with detached legs 3, the device can also be designed so that the adjustable anti-reversing portions 19 rotate in a direction to move the device's legs 3 farther apart for distraction of bone fragments.

Figure 45A:
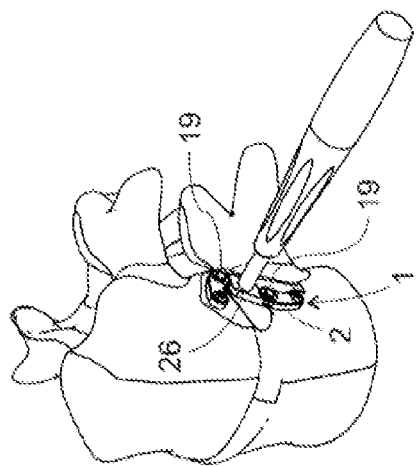
FIGS. 45A-45D illustrate insertion of a surgical device having two adjustable anti-reversing portions for both compression and distraction according to the present invention.
Figure 45B:
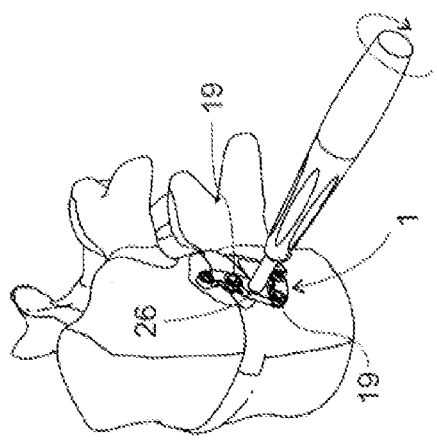
Figure 45C:
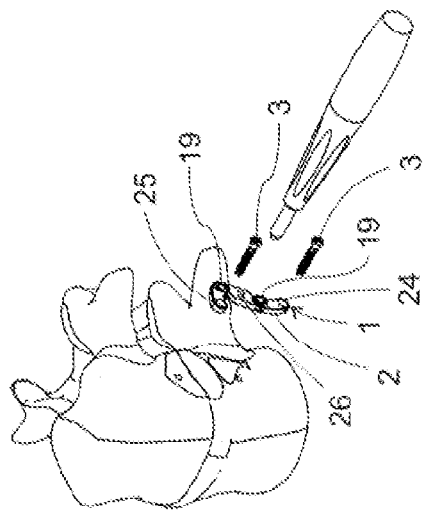
Figure 45D:
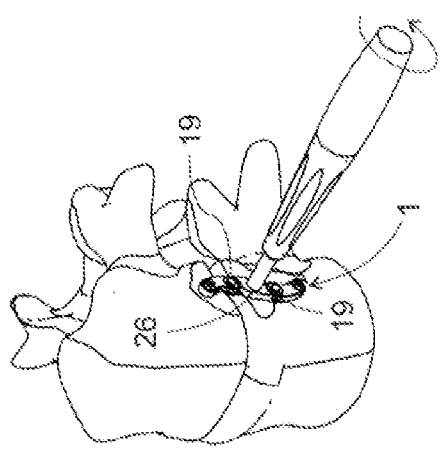

As shown in FIGS. 45A-45D, the device can be used for both compression and distraction of bones, tissues, or fragments thereof at the same time. The user can insert an instrument that is designed to fit the aperture 26 between the two adjustable anti-reversing portions 19, turn the instrument in one direction to rotate one adjustable anti-reversing portion 19 and leg 3 in an anti-reversing direction for distraction, as shown in FIG. 45C, and turn the instrument in the opposite direction to rotate the other adjustable anti-reversing portion 19 and leg 3 in an anti-reversing direction for compression, as shown in FIG. 45D.

Figure 40A:
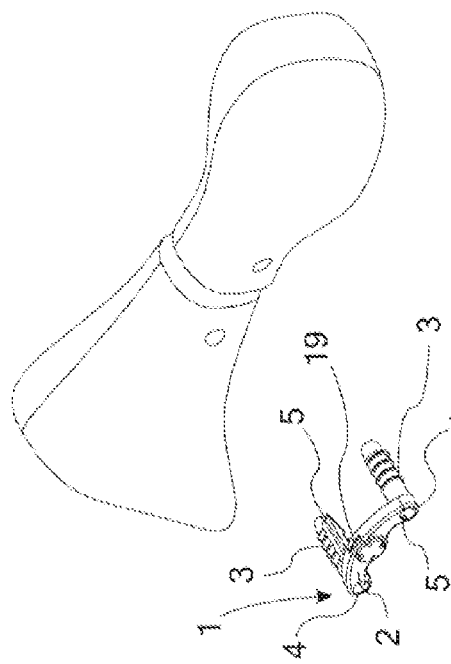
FIGS. 40A-40C illustrate insertion of a surgical device having one symmetrically-positioned adjustable anti-reversing portion for compression according to the present invention.
Figure 40B:
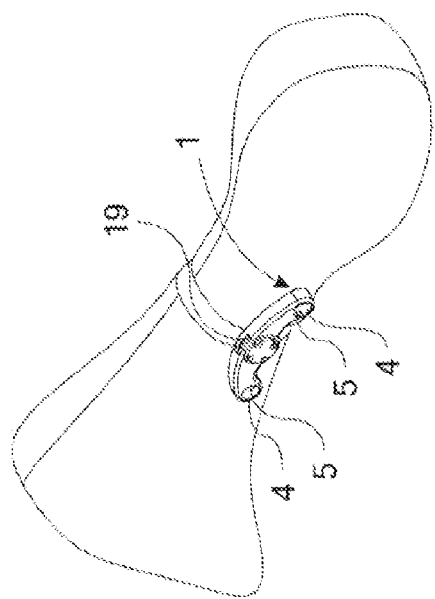
Figure 40C:
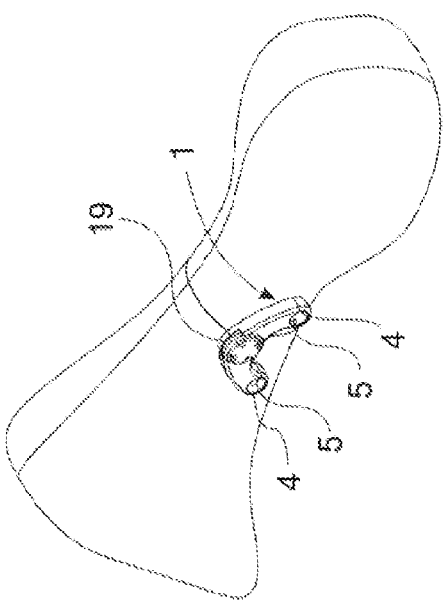
Figure 41A:
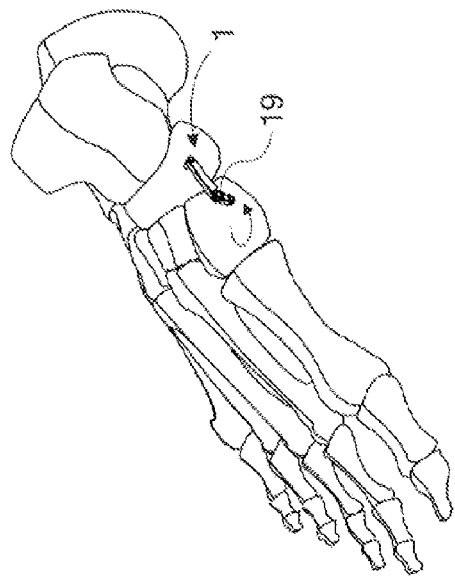
FIGS. 41A-41C illustrate insertion of a surgical device having one asymmetrically-positioned adjustable anti-reversing portion for compression according to the present invention.
Figure 41B:
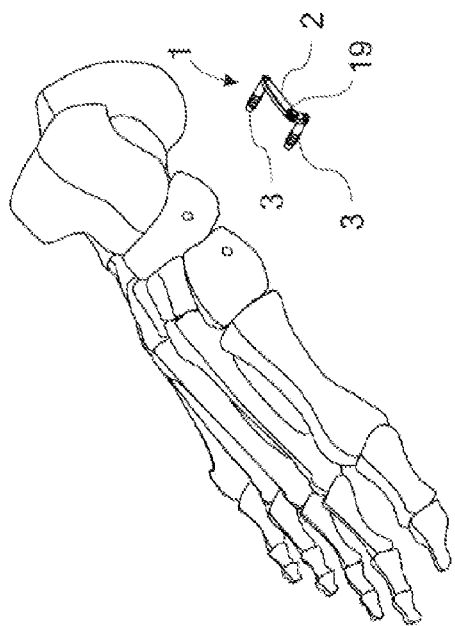
Figure 41C:
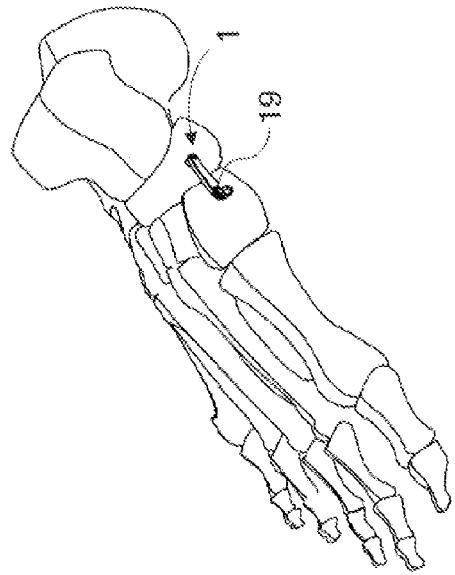
Figure 42A:
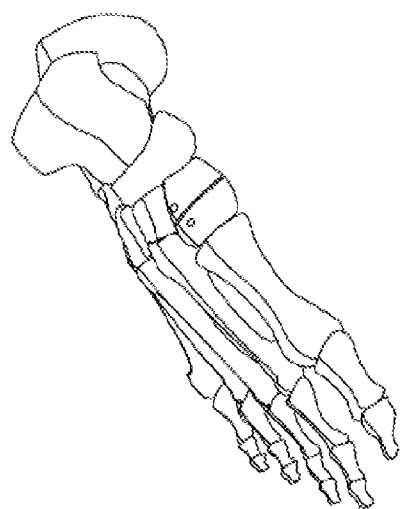
FIGS. 42A-42D illustrate insertion of device having one symmetrically-positioned adjustable anti-reversing portion for distraction according to the present invention.
Figure 42B:
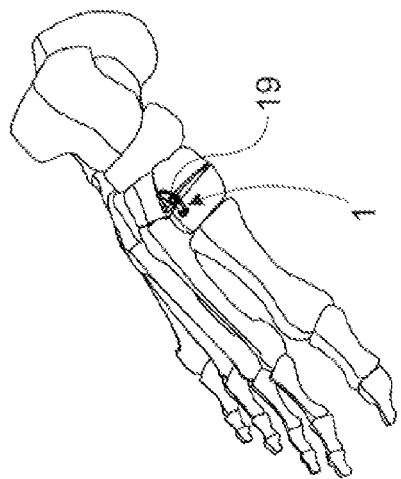
Figure 42C:
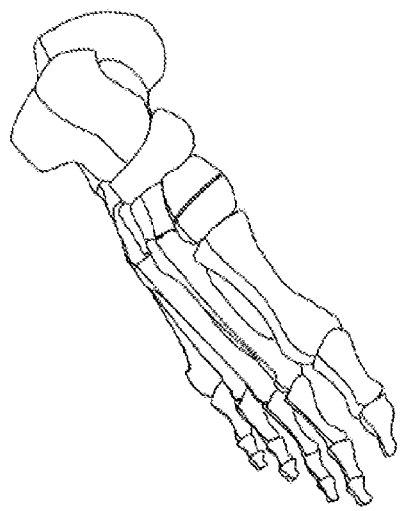
Figure 42D:
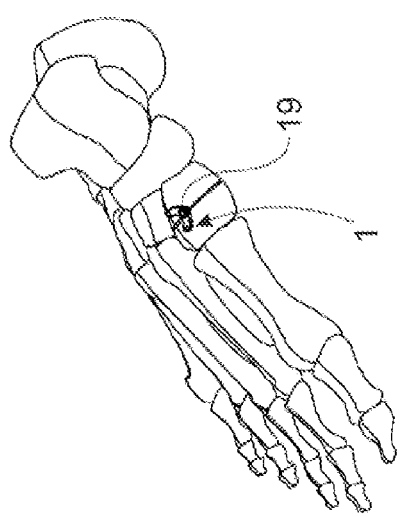

FIGS. 40A-C illustrate use of the device 1 having one symmetrically-positioned adjustable anti-reversing portion 19 for compression. FIGS. 41A-C illustrate use of the device 1 having one asymmetrically-positioned adjustable anti-reversing portion 19 for compression. FIGS. 42A-D illustrate uses of the device 1 having one symmetrically-positioned adjustable anti-reversing portion 19 for distraction. The practitioner can adjust the adjustable anti-reversing portion(s) 19 by adjusting the bridge 2, device's legs 3, or by inserting an instrument that fits into aperture(s) 27 of the adjustable anti-reversing portion(s) 19 and turning the instrument to rotate the adjustable anti-reversing portion(s) 19 in a one-way direction for compression or distraction. The apertures 27 can be designed in any shape to correspond with the instrument that is used to rotate the adjustable anti-reversing portion(s) 19 via insertion in the aperture(s) 27.

Figure 43A:
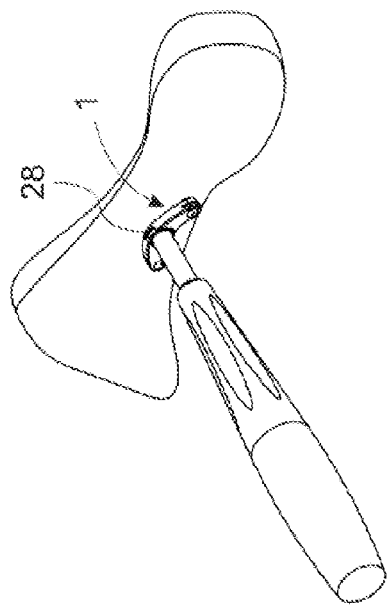
FIGS. 43A-43D illustrate removal of device having one symmetrically-positioned adjustable anti-reversing portion according to the present invention.
Figure 43B:
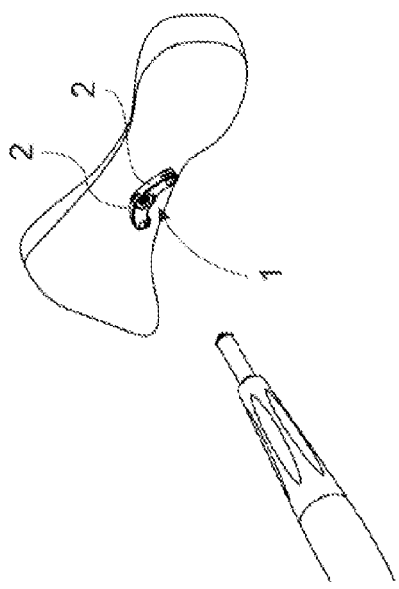
Figure 43C:
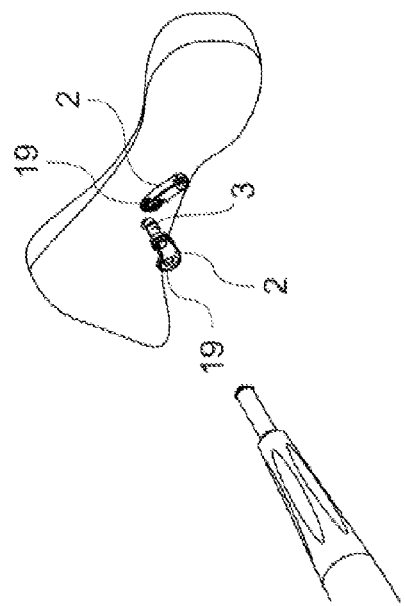
Figure 43D:
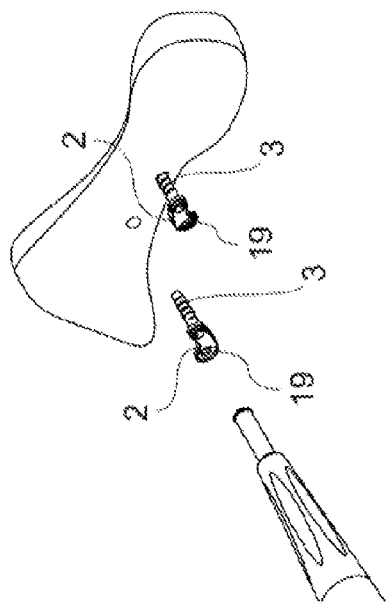

The device can be easily removed, as shown by a non-limiting example in FIGS. 43A-D. As shown in FIGS. 14, 20, 28, and 43A-D, the device's bridge 2 can be comprised more than one bridge portions 2 and can include assembly screw(s) 28. An instrument can be inserted into the assembly screw 28 to turn the assembly screw 28 in a direction for its removal, as illustrated in FIG. 43A. Once the assembly screw 28 is removed from the device as shown in FIG. 43B, the bridge 2 can separate into the two bridge portions 2. As shown in FIGS. 43C-D, each device leg 3 can then be individually removed by rotating each leg 3, one at a time, out of the bone.

Likewise, the device 1 having a bridge 2 with detached legs 3 can also be easily removed. This embodiment does not require removal via an assembly screw 28. First, each leg 3, or bone screw, can be removed from the bone. Second, the remaining component of the device 1, the bridge 2, is thereby removed because it is no longer attached with the bone via the legs 3. These in vivo disassemblies of the device 1 allow for easy and non-destructive removal of the device 1, compared to many devices in the prior art which include barbed legs and require significant bone destruction for their removal.

Figure 46A:
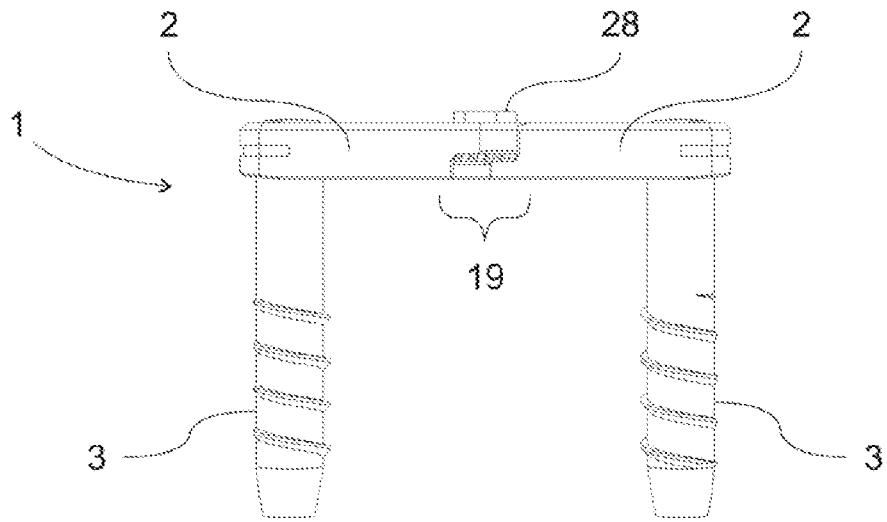
FIGS. 46A and 46B are front perspective views of a surgical device having one symmetrically-positioned adjustable anti-reversing portion according to the present invention.
Figure 46B:
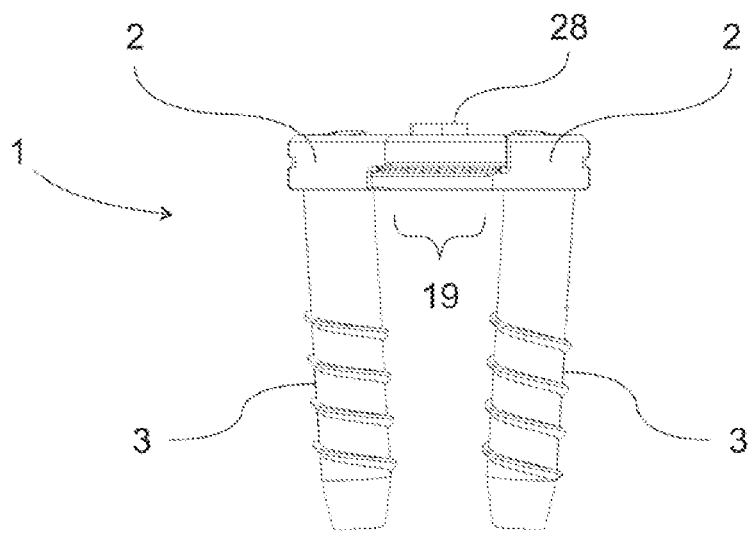

The legs 3 of the device 1 having a bridge 2 with adjustable anti-reversing portion(s) 19 can be designed to converge at the distal end of the legs 3 upon compression or distraction. For example, as shown in FIG. 46A, the legs 3 of the device before compression can be positioned at ninety-degree (90°) angles from the bridge 2. Upon compression, as shown in FIG. 46B, the ends of the legs 3 farthest from the bridge 2 will converge toward one another so that the legs 3 will each form an angle with the bridge 2 that is less than ninety degrees (90°). The converged legs 3 allow for even compression of the entire device 1, from the bridge 2 of the device 1, along the length of the device's legs 3, to the distal end of the device's legs 3. The converged legs 3 allow for maximum compression throughout the device 1 and into the bone, e.g., the far cortex of an osteotomy or fracture, instead of merely at the top of the bone. The legs 3 can also remain at ninety-degree angles from the bridge 2 and not converge upon compression of the device 1. Likewise, the legs 3 can converge at their distal ends farthest from the bridge 2 upon distraction of the device 1, or can remain at ninety-degree (90°) angles from the bridge 2 upon distraction of the device 1.

The device 1 with a bridge 2 having adjustable anti-reversing portion(s) 19 can be made with the device's legs 3 in various lengths and the device's bridge 2 in various lengths. As a non-limiting example, the device's legs 3 can vary in length from five (5.0) to twenty-five (25) millimeters and vary in diameter from two (2) to three and eight-tenths (3.8) millimeters. Non-limiting examples of the range of motion during compression and distraction are shown in Table 1 below.

TABLE 1

Device Interaxis Travel Data (mm)

| Device Embodiment | Device size | First Position | End of Travel | Total Travel |
|---|---|---|---|---|
| One Symmetrical Adjustable Anti-reversing Portion | 07 | 7.5 | 2.5 | 5 |
| | 09 | 9 | 3.3 | 5.7 |
| | 11 | 11 | 4.4 | 6.6 |
| | 13 | 13 | 5.5 | 7.5 |
| | 15 | 15 | 6 | 9 |
| | 20 | 20 | 8.5 | 11.5 |
| One Asymmetrical Adjustable Anti-reversing Portion: | 20 | 20 | 14 | 6 |
| | 25 | 25 | 19 | 6 |
| | 30 | 30 | 24 | 6 |
| Two Adjustable Anti-reversing Portions: | 20 | 20 | 6.7 | 13.3 |
| | 25 | 25 | 10.4 | 14.6 |
| | 30 | 30 | 15 | 15 |

The surgical device 1 can create compression by adjusting the adjustable anti-reversing portion(s) 19 with the anti-reversing mechanism. The range of movement is based on the device's size and the amount of compression is based on the amount a user adjusts the adjustable anti-reversing portion(s) 19. For example, the range of compression for a device 1 with an inter-axis size of five (5.0) millimeters to thirteen and a half (13.5) millimeters can be between zero (0) to thirty-five (35) pounds. The device 1 can be designed for compression of larger areas, i.e., twenty-five (25) millimeters and above.

Compression staples known in the prior art do not supply a known amount of compression force. Further, studies indicate that standard diamond-type staples return to zero compression after ten minutes of compression. The device 1 described herein can lock into position without the need for additional instrumentation and will maintain compression better than nitinol (memory wire), which holds seven (7) pounds of compression. Tested at twenty (20) pounds, the device locks into position with an initial reduction of zero (0) to one-half (0.5) pounds and maintains compression with a reduction over a ten-day period of only one and a quarter (1.25) pounds.

The device 1 described herein can be used for, but is not limited to, the following indications: osteotomy fixation, arthrodesis, and bone fragment fixation; proximal tibial metaphysis osteotomy fixation; adjunctive fixation of small bone fragments in the humerus, ulna, radius, femur, fibula, tibia, clavicle, ribs, pelvis, scapula, and sternum; fixation of soft tissue to bone such as anterior cruciate ligament (ACL) reconstruction, fixation of maxillofacial and mandibulofacial fractures and osteotomies; fixation of unloaded craniofacial bone fractures and cranioplasties; spine fusion/fixation and epiphysiodeses in pediatric reconstruction; sternotomy closure; and open wedge procedures such as first metatarsal osteotomy. The device 1 is needed in certain areas of the anatomy, such as around the short, compact tarsal bones and their respective joints.

Figure 44:
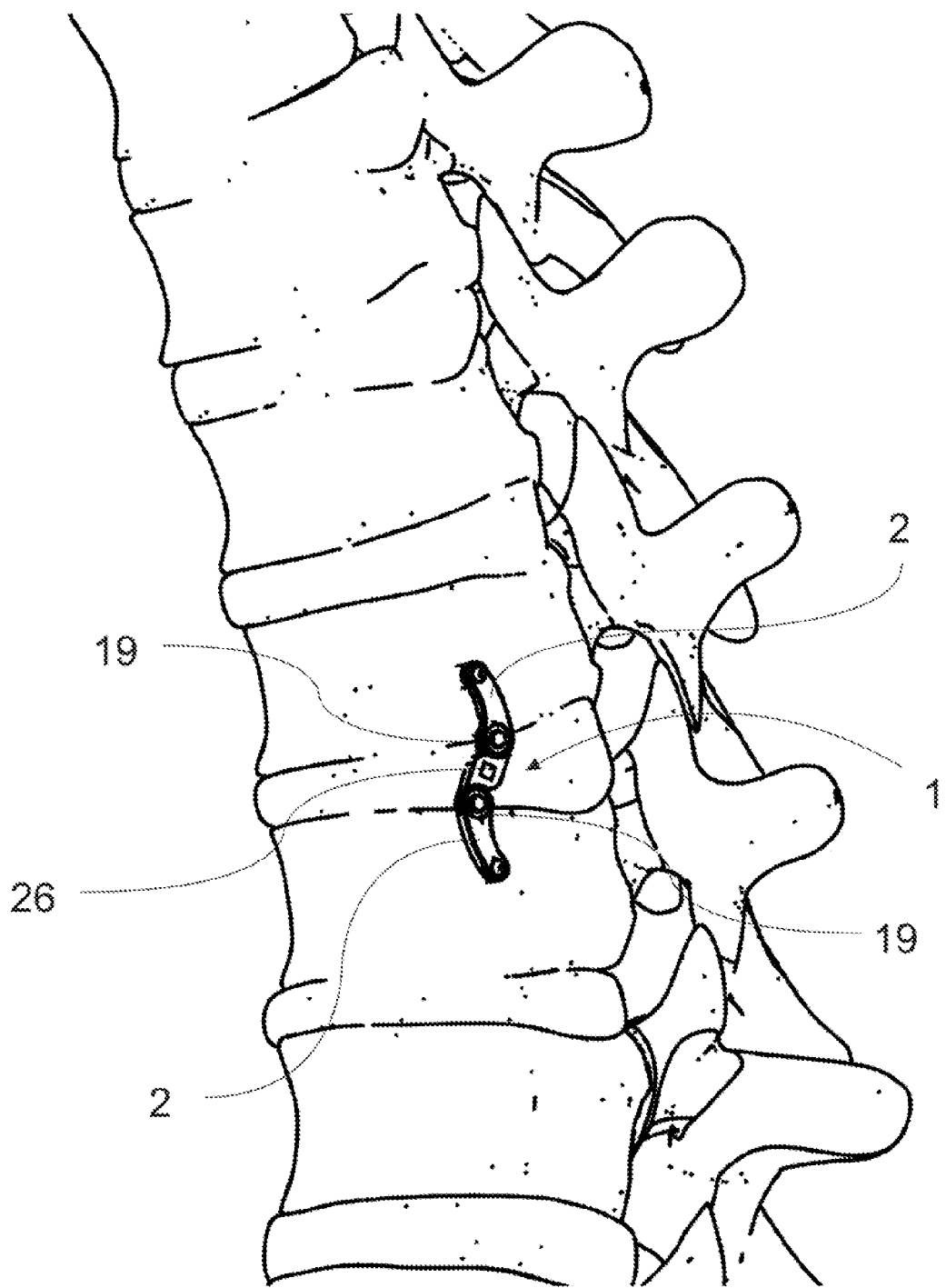
FIG. 44 is a front perspective view of a surgical device used in a spinal application according to the present invention.

The compression devices 1 described herein provide for easy methods of obtaining and maintaining excellent compression and rigid internal fixation while obviating the need for excessive dissection and/or the need to violate neighboring joints or soft tissues. The device 1 can also be used for compression or distraction of the spine, as well as any other part of the anatomy that requires compression or distraction. A non-limiting example of the surgical device used for the spine is shown by FIG. 44.

The device 1 including adjustable anti-reversing portion(s) 19 can be made from any metallic steel or titanium material, as well as those materials used for the surgical staple without adjustable anti-reversing portion(s). The device 1 having a bridge 2 with adjustable anti-reversing portion(s) 19 can be used with the surgical device system described herein. The device 1 having a bridge 2 with adjustable anti-reversing portion(s) 19 can also be installed using the method described herein that is used with the staple without adjustable anti-reversing portions. The device system and method described which utilizes guide wires 7 allows for quicker and more accurate placement of the devices in surgical procedures.

While the foregoing describes the present invention in relation to illustrations and examples, it is understood that it is not intended to limit the scope of the invention to the illustrations and examples described herein. On the contrary, it is intended to cover all alternative modifications and equivalents that may be included in the spirit and the scope of the invention as defined by the appended claims.

What is claimed is:

1. A surgical device for compression or distraction of a first body part relative to a second body part, comprising:
   a bridge having a first aperture and a second aperture and at least one adjustable anti-reversing portion between said first and second apertures, said adjustable anti-reversing portion separating said bridge into a first section and a second section;
   a first leg and second leg, wherein said first leg is capable of being inserted through said first aperture and into said first body part, and said second leg is capable of being inserted through said second aperture and into said second body part;

said adjustable anti-reversing portion allowing said first and second sections of said bridge to rotate relative to each other in one direction, but not in a reverse direction;

wherein said first section of said bridge, said second section of said bridge, and said adjustable anti-reversing portion are coplanar with each other along a plane perpendicular to said first and second legs;

wherein rotation of said first section of said bridge relative to said second section of said bridge maintains a coplanar relationship between said first section of said bridge and said second section of said bridge, and rotation of said first section of said bridge relative to said second section of said bridge maintains a perpendicular relationship between said bridge and each of said first and second legs;

wherein said adjustable anti-reversing portion permits rotation between said first and second sections of said bridge along said plane, thereby permitting a user to adjust a relative angle and distance between said first and second legs;

whereby said surgical device is capable of providing compression or distraction of said first body part relative to said second body part when said at least one adjustable anti-reversing portion is adjusted.

2. The surgical device of claim 1, wherein said at least one adjustable anti-reversing portion is selected from the group consisting of a hinged system, a one-way sliding track system, a ratchet system, a gear and pawl system, a rack and pinion system, and a one-way clutch system.

3. The surgical device of claim 1, wherein each said first leg and said second leg further comprises an aperture extending axially therethrough;

whereby said first leg and said second leg are capable of receiving a guide wire such that said first and second legs are guided by said guide wires when a user inserts said first and second legs over said guide wires, through said first and second apertures of said device, and into said first body part and said second body part.

4. A surgical device system comprising:
the surgical device of claim 3;
a first guide wire;
a second guide wire; and
a drill, wherein said drill further comprises a drill bit having an axial aperture therethrough and is capable of receiving a guide wire therethrough;

whereby a user can insert said first guide wire into a first body part and said second guide wire into a second body part, bore a hole around each said first and second guide wires and into said first and second body parts, insert said first aperture and said second aperture of said bridge over said first and second guide wires, insert each of said first and second legs over said first and second guides wires, through said first aperture and said second aperture of said bridge and into said holes in said first and second body parts, thereby inserting said surgical device into said first and second body parts.

5. The surgical device of claim 1, wherein said device comprises two adjustable anti-reversing portions; and said bridge further comprises an aperture positioned between said two adjustable anti-reversing portions, wherein said aperture positioned between said two adjustable anti-reversing portions is capable of receiving an instrument therethrough, whereby a user can insert said instrument into said aperture positioned between said two adjustable anti-reversing portions and thereby cause said adjustable anti-reversing portions to provide compression or distraction of said first body part relative to said second body part.

6. A method for the compression or distraction of a first body part relative to a second body part, comprising the acts of: inserting the surgical device of claim 1 into said first body part and said second body part; and adjusting said at least one adjustable anti-reversing portion to provide compression or distraction of said first body part relative to said second body part.

7. The surgical device of claim 1, wherein said adjustable anti-reversing portion provides a known amount of compression when said adjustable anti-reversing portion is adjusted to provide compression of said first body part relative to said second body part.

8. The surgical device of claim 1, wherein said legs converge toward one another upon compression or distraction of said device.

9. A surgical device for compression or distraction of a first body part relative to a second body part, comprising:
a bridge having a first leg and a second leg extending from a same side of said bridge, wherein said first leg is capable of being inserted into said first body part and said second leg is capable of being inserted into said second body part, and wherein said bridge further comprises at least one adjustable anti-reversing portion, said adjustable anti-reversing portion separating said bridge into a first section and a second section;

said adjustable anti-reversing portion allowing said first and second sections of said bridge to rotate relative to each other in one direction, but not in a reverse direction, on a plane that is perpendicular to said legs;

wherein said first section of said bridge, said second section of said bridge, and said adjustable anti-reversing portion are coplanar with each other along said plane perpendicular to said first and second legs;

wherein rotation of said first section of said bridge relative to said second section of said bridge maintains a coplanar relationship between said first section of said bridge and said second section of said bridge, and rotation of said first section of said bridge relative to said second section of said bridge maintains a perpendicular relationship between said bridge and each of said first and second legs;

wherein said adjustable anti-reversing portion permits rotation between said first and second sections of said bridge along said plane, thereby permitting a user to adjust a relative angle and distance between said first and second legs;

whereby said surgical device is capable of providing compression or distraction of said first body part relative to said second body part when said at least one adjustable anti-reversing portion is adjusted.

10. The surgical device of claim 9, wherein said at least one adjustable anti-reversing portion is selected from the group consisting of a hinged system, a one-way sliding track system, a ratchet system, a gear and pawl system, a rack and pinion system, and a one-way clutch system.

11. The surgical device of claim 9, wherein each said first and second leg further comprises at least an inner elevation and an outer elevation along the length of each said first and second leg;

whereby said first and second legs are capable of receiving a guide wire between said inner and said outer elevations such that said first and second legs are guided by said guide wires when a user inserts said first and second legs over said guide wires and into said first body part and said second body part.

12. A surgical device system comprising:
the surgical device of claim 11;
a first guide wire;
a second guide wire; and
a drill, wherein said drill further comprises a drill bit having an axial aperture therethrough and is capable of receiving a guide wire therethrough;
whereby a user can insert said first guide wire into a first body part and said second guide wire into a second body part, bore a hole around each said first and second guide wires and into said first and second body parts, insert each of said first and second legs over said first and second guides wires and into said holes in said first and second body parts, thereby inserting said surgical device into said first and second body parts.

13. The surgical device of claim 9, wherein each said first leg and said second leg further comprises an aperture extending axially therethrough;
whereby said first leg and said second leg are capable of receiving a guide wire such that said first and second legs are guided by said guide wires when a user inserts said first and second legs over said guide wires and into said first body part and said second body part.

14. A surgical device system comprising:
the surgical device of claim 13;
a first guide wire;
a second guide wire; and
a drill, wherein said drill further comprises a drill bit having an axial aperture therethrough and is capable of receiving a guide wire therethrough;
whereby a user can insert said first guide wire into a first body part and said second guide wire into a second body part, bore a hole around each said first and second guide wires and into said first and second body parts, insert each of said first and second legs over said first and second guides wires and into said holes in said first and second body parts, thereby inserting said surgical device into said first and second body parts.

15. The surgical device of claim 9, wherein said device comprises two adjustable anti-reversing portions; said bridge further comprises an aperture positioned between said two adjustable anti-reversing portions, wherein said aperture positioned between said two adjustable anti-reversing portions is capable of receiving an instrument therethrough;
whereby a user can insert said instrument into said aperture positioned between said two adjustable anti-reversing portions and thereby cause said adjustable anti-reversing portions to provide compression or distraction of said first body part relative to said second body part.

16. The surgical device of claim 9, wherein said at least one adjustable anti-reversing portion further comprises at least one aperture, wherein said at least one aperture of said at least one adjustable anti-reversing portion is capable of receiving an instrument;
whereby a user can insert said instrument into said at least one aperture of said at least one adjustable anti-reversing portion and thereby cause said at least one adjustable anti-reversing portion to provide compression or distraction of said first body part relative to said second body part.

17. The surgical device of claim 9, wherein said bridge further comprises:
more than one bridge portions, wherein said first leg is attached to one of said more than one bridge portions and said second leg is attached to one of said more than one bridge portions; and
at least one assembly screw, wherein said at least one assembly screw attaches said more than one bridge portions with one another,
whereby a user can remove said assembly screw to separate said bridge into said more than one bridge portions and subsequently remove each said first and second legs from said first and second body parts to thereby remove said device from said body parts.

18. A method for the compression or distraction of a first body part relative to a second body part, comprising the acts of: inserting the surgical device of claim 9 into said first body part and said second body part; and adjusting said at least one adjustable anti-reversing portion to provide compression or distraction of said first body part relative to said second body part.

19. The surgical device of claim 9, wherein said adjustable anti-reversing portion provides a known amount of compression when said adjustable anti-reversing portion is adjusted to provide compression of said first body part relative to said second body part.

20. The surgical device of claim 9, wherein said legs converge toward one another upon compression or distraction of said device.

21. The surgical device of claim 9, wherein said bridge further comprises:
more than one bridge portions, wherein said first leg is attached to one of said more than one bridge portions and said second leg is attached to one of said more than one bridge portions; and
at least one connecting element, wherein said at least one connecting element attaches said more than one bridge portions with one another and simultaneously allows said more than one bridge portions to move with respect to one another when said at least one adjustable anti-reversing portion is adjusted for compression or distraction.

* * * * *